(12) United States Patent
Eliu et al.

(10) Patent No.: US 7,091,358 B2
(45) Date of Patent: Aug. 15, 2006

(54) CATIONIC SUBSTITUTED HYDRAZONE DYES

(75) Inventors: Victor Paul Eliu, Lörrach (DE); Beate Fröhling, Steinen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 336 days.

(21) Appl. No.: 10/778,478

(22) Filed: Feb. 12, 2004

(65) Prior Publication Data
US 2004/0158937 A1 Aug. 19, 2004

(30) Foreign Application Priority Data
Feb. 17, 2003 (EP) .................................. 03405093

(51) Int. Cl.
*C09B 26/04* (2006.01)
*A61Q 5/10* (2006.01)

(52) U.S. Cl. .............................. 546/332; 8/405; 8/406; 8/407; 8/408; 8/426

(58) Field of Classification Search ................ 546/332; 8/405, 406, 407, 408, 426
See application file for complete search history.

(56) References Cited

U.S. PATENT DOCUMENTS

| | | | | |
|---|---|---|---|---|
| 3,158,608 | A | * 11/1964 | Raue | 546/104 |
| 4,026,885 | A | * 5/1977 | Frey et al. | 546/9 |
| 4,424,349 | A | * 1/1984 | Giesecke | 546/9 |
| 5,919,273 | A | 7/1999 | Rondeau et al. | 8/412 |
| 6,432,146 | B1 | 8/2002 | Rondeau | 8/407 |
| 2005/0000034 | A1* | 1/2005 | Eliu et al. | 8/405 |

FOREIGN PATENT DOCUMENTS

| | | |
|---|---|---|
| EP | 0850636 | 7/1998 |
| EP | 1025834 | 8/2000 |
| EP | 1153599 | 11/2001 |
| EP | 1166752 | 1/2002 |
| WO | 95/01772 | 1/1995 |
| WO | 95/15144 | 6/1995 |
| WO | 99/20234 | 4/1999 |
| WO | 00/10519 | 3/2000 |
| WO | 00/12057 | 3/2000 |

* cited by examiner

*Primary Examiner*—Fiona T. Powers
(74) *Attorney, Agent, or Firm*—Kevin T. Mansfield

(57) ABSTRACT

The present invention relates to novel cationic dyes of formula (1), (2) or (3)

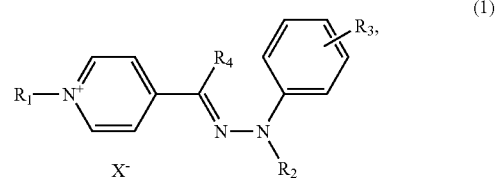

(1)

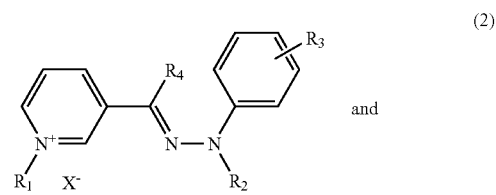

(2)
and

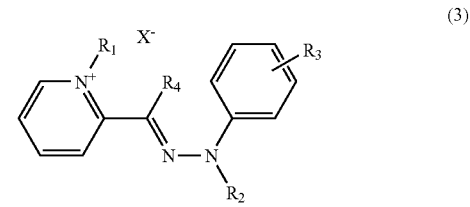
(3)

wherein $R_1$ and $R_2$ are each independently of the other a $C_1$–$C_8$alkyl radical or an unsubstituted or substituted benzyl radical, $R_3$ is hydrogen, $C_1$–$C_8$alkyl, $C_1$–$C_8$alkoxy, cyanide or halide, and $R_4$ is a $C_1$–$C_8$alkyl radical or an unsubstituted or substituted aryl radical, and $X^-$ is an anion. Further, the present invention relates to compositions thereof, especially comprising other dyes, to processes for the preparation thereof and to the use thereof in the dyeing of organic material, such as keratin fibers, especially hair; or wool, leather, silk, cellulose or polyamides, and preferably human hair.

13 Claims, No Drawings

CATIONIC SUBSTITUTED HYDRAZONE DYES

The present invention relates to novel cationic dyes, compositions thereof, to processes for their preparation and to their use in the dyeing of organic material, such as keratin fibres, wool, leather, silk, cellulose or polyamides, especially keratin-containing fibres, colton or nylon, and preferably hair, more preferably human hair.

It is known, for example, from WO 95/01772, WO 95/15144, EP 714 954 and EP 318 294 that cationic dyes can be used to dye organic material, for example keratin, silk, cellulose or cellulose derivatives, and also synthetic fibres, for example polyamides. Cationic dyes exhibit very brilliant shades. A disadvantage is their unsatisfactory fastness to hydrolysis and to light, their frequently inadequate stability under reducing or oxidising conditions, and their frequently unsatisfactory storage stability (see: John F. Corbett: "The Chemistry of Hair-Care Products", JSCD August 1976, page 290).

The actual technical problem of the present invention was to provide brilliant dyes that are distinguished by deep dying having good fastness properties with respect to washing, light, shampooing and rubbing, and that preferably exhibit satisfactory stability under reducing or oxidising dyeing conditions, for the dyeing of organic material.

Accordingly, the cationic dyes of formula (1), (2) or (3)

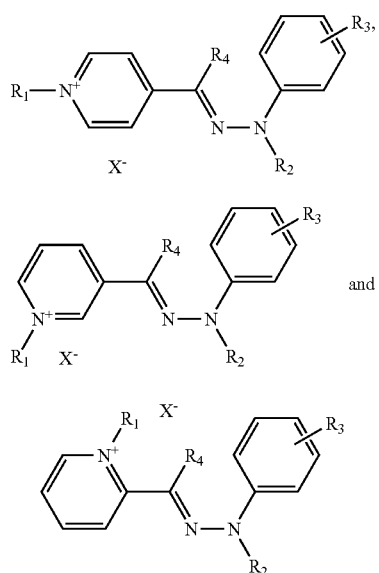

have been discovered, wherein
$R_1$ and $R_2$ are each independently of the other a $C_1$–$C_8$alkyl radical or an unsubstituted or substituted benzyl radical,
$R_3$ is hydrogen, $C_1$–$C_8$alkyl, $C_1$–$C_8$alkoxy, cyanide or halide, preferably hydrogen, and
$R_4$ is a $C_1$–$C_8$alkyl radical or an unsubstituted or substituted aryl radical, and
$X^-$ is an anion.

In the present invention, substituents of aryl, especially benzyl, or heterocyclic organic radical are, for example $C_1$–$C_8$alkyl, $C_1$–$C_8$alkoxy, cyanide and/or halide.

The alkyl radical is, for example, $C_1$–$C_8$alkyl, preferably $C_1$–$C_4$alkyl, and may be straight-chain, branched, substituted or unsubstituted, or, from $C_5$alkyl upwards, monocyclic or polycyclic, and may be uninterrupted or interrupted by hetero atoms, such as O, S, N, NH.

$C_1$–$C_8$alkyl is, for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl.

$C_1$–$C_4$alkyl is, for example, methyl, ethyl, propyl, isopropyl, n-butyl, sec-butyl or tert-butyl.

$C_1$–$C_8$alkoxy is O—$C_1$–$C_8$alkyl, preferably O—$C_1$–$C_4$alkyl.

Aryl radical is, for example, a phenyl-, benzyl-, tolyl radical or a substituted or unsubstituted heterocyclic organic radical.

Heterocyclic organic radical is, for example, a five-membered nitrogen-containing heterocyclic radical such as imidazolyl, pyrazolyl, triazolyl, pyrrolyl, pyrrolidinyl, oxazolyl or thiazolyl, a six-membered nitrogen-containing heterocyclic radical such as piperazinyl, piperidinyl, pyridinyl or morpholinyl, or a bicyclic radical which possesses a fused-on five-membered nitrogen-containing heterocycle and a six-membered aromatic ring, such as benzoxazolyl, indolyl, benzothiazolyl, benzimidazolyl or benzotriazolyl.

Halide is, for example, fluoride, chloride, bromide or iodide, especially chloride and fluoride.

"Anion" denotes, for example, an organic or inorganic anion, such as halide, preferably chloride, iodide and fluoride, sulfate, hydrogen sulfate, phosphate, boron tetrafluoride, carbonate, bicarbonate, oxalate or $C_1$–$C_8$alkyl sulfate, especially methyl sulfate or ethyl sulfate; anion also denotes lactate, formate, acetate, propionate or a complex anion, such as the zinc chloride double salt.

The anion is especially a halide, preferably chloride or fluoride, sulfate, hydrogen sulfate, methyl sulfate, phosphate, formate, acetate or lactate.

The anion is more especially chloride, iodide, methyl sulfate, formate or acetate.

Preference is given to yellow cationic dyes of formula (1), (2) or (3) of the present invention wherein
$R_1$ and $R_2$ are each independently of the other a methyl radical or an unsubstituted or substituted benzyl radical, More preference is given especially to cationic dyes of formula (1), (2) or (3) wherein
$R_1$ and $R_2$ are each independently of the other a methyl radical or an unsubstituted or substituted benzyl radical, and
$R_4$ is a $C_1$–$C_8$alkyl radical.

Most preference is given especially to cationic dyes of formula (4), (5'), (6), (7), (8), (9), (10), (11), (12), (13) or (14)

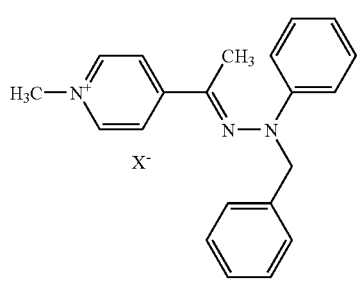

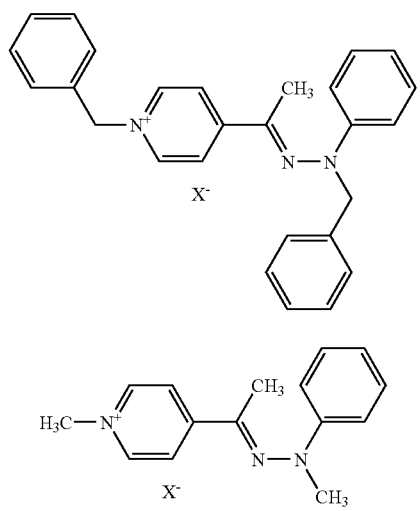
(5')
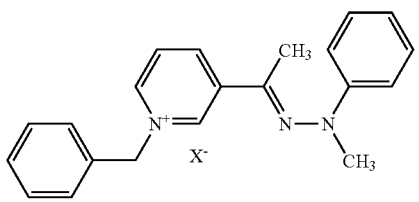
(10)
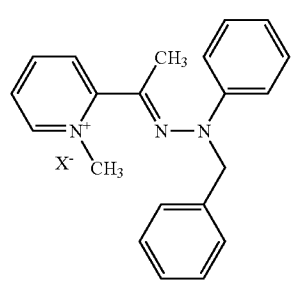
(11)
(5)
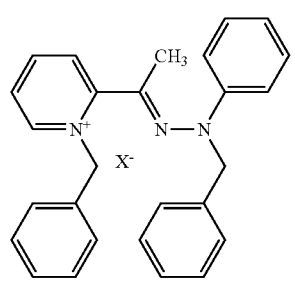
(12)
(6)
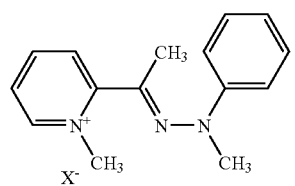
(13)
(7)
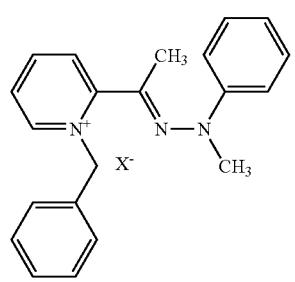
(14)
(8)
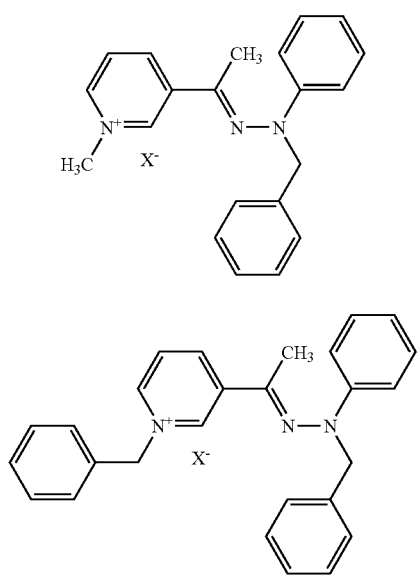
(9)
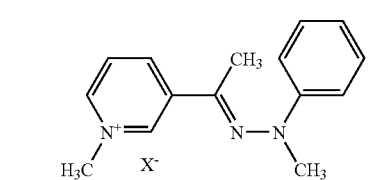
wherein
X⁻ is an anion.
Preferably, the anion in the compounds of formula (4), (5'), (6), (7), (8), (9), (10), (11), (12), (13) or (14) is chloride, iodide, methyl sulfate, formate or acetate.
The present invention relates also to a process for the preparation of the dyes of formula (1), (2) or (3), preferably to a dye of formula (4), (5'), (6), (7), (8), (9), (10), (11), (12), (13), or (14), and comprises reacting a phenylhydrazine of formula (15)

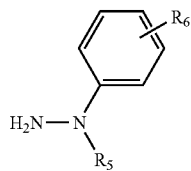

(15)

wherein
  $R_5$ is hydrogen, a $C_1$–$C_8$alkyl radical or an unsubstituted or substituted benzyl radical and
  $R_6$ is hydrogen, $C_1$–$C_8$alkyl, $C_1$–$C_8$alkoxy, cyanide or halide, preferably hydrogen, with a
a) 4-pyridylketone of formula (16)

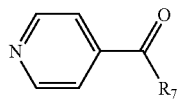

(16)

wherein
  $R_7$ is a $C_1$–$C_8$alkyl radical or an unsubstituted or substituted aryl radical to form a hydrazone of formula (17)

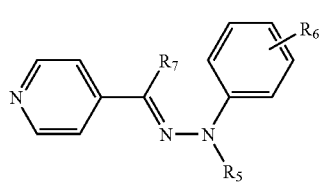

(17)

$R_5$ is hydrogen, a $C_1$–$C_8$alkyl radical or an unsubstituted or substituted benzyl radical,
  $R_6$ is hydrogen, $C_1$–$C_8$alkyl, $C_1$–$C_8$alkoxy, cyanide or halide, preferably hydrogen, and
  $R_7$ is a $C_1$–$C_8$alkyl radical or an unsubstituted or substituted aryl radical and
then reacting the latter compound of formula (17) with an alkylating or benzylating agent to form a compound of formula (1)

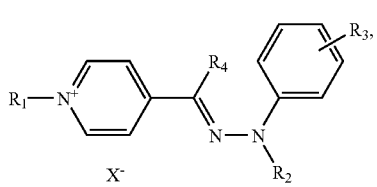

(1)

wherein
  $R_1$ and $R_2$ are each independently of the other a $C_1$–$C_8$alkyl radical or an unsubstituted or substituted benzyl radical,
  $R_3$ is hydrogen, $C_1$–$C_8$alkyl, $C_1$–$C_8$alkoxy, cyanide or halide, preferably hydrogen, and
  $R_4$ is a $C_1$–$C_8$alkyl radical or an unsubstituted or substituted aryl radical, and
  $X^-$ is an anion; or, which process comprises reacting a phenylhydrazine of formula (15) with
b) 3-pyridylketone of formula (18)

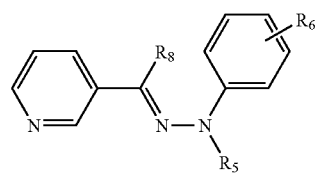

(18)

wherein
  $R_8$ is a $C_1$–$C_8$alkyl radical or an unsubstituted or substituted aryl radical to form a hydrazone of formula (19)

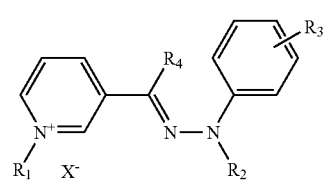

(19)

$R_5$ is hydrogen, a $C_1$–$C_8$alkyl radical or an unsubstituted or substituted benzyl radical,
  $R_6$ is hydrogen, $C_1$–$C_8$alkyl, $C_1$–$C_8$alkoxy, cyanide or halide, preferably hydrogen, and
  $R_8$ is a $C_1$–$C_8$alkyl radical or an unsubstituted or substituted aryl radical and
then reacting the latter compound of formula (19) with an alkylating or benzylating agent to form a compound of formula (2)

(2)

wherein
  $R_1$ and $R_2$ are each independently of the other a $C_1$–$C_8$alkyl radical or an unsubstituted or substituted benzyl radical,
  $R_3$ is hydrogen, $C_1$–$C_8$alkyl, $C_1$–$C_8$alkoxy, cyanide or halide, preferably hydrogen, and
  $R_4$ is a $C_1$–$C_8$alkyl radical or an unsubstituted or substituted aryl radical, and
  $X^-$ is an anion; or, which process comprises reacting a phenylhydrazine of formula (15) with c) 2-pyridylketone of formula (20)

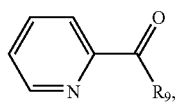
(20)

wherein $R_9$ is a $C_1$–$C_8$alkyl radical or an unsubstituted or substituted aryl radical to form a hydrazone of formula (21)

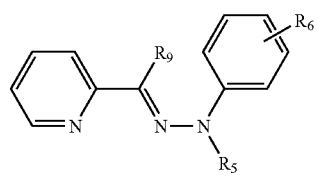
(21)

$R_5$ is hydrogen, a $C_1$–$C_8$alkyl radical or an unsubstituted or substituted benzyl radical, $R_6$ is hydrogen, $C_1$–$C_8$alkyl, $C_1$–$C_8$alkoxy, cyanide or halide, preferably hydrogen, and $R_9$ is hydrogen, a $C_1$–$C_8$alkyl radical or an unsubstituted or substituted aryl radical and then reacting the latter compound of formula (21) with an alkylating or benzylating agent to form a compound of formula (3)

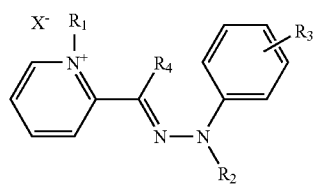
(3)

wherein $R_1$ and $R_2$ are each independently of the other a $C_1$–$C_8$alkyl radical or an unsubstituted or substituted benzyl radical, $R_3$ is hydrogen, $C_1$–$C_8$alkyl, $C_1$–$C_8$alkoxy, cyanide or halide, preferably hydrogen, and $R_4$ is a $C_1$–$C_8$alkyl radical or an unsubstituted or substituted aryl radical, and $X^-$ is an anion.

The reaction is generally initiated by bringing the phenylhydrazine (15) and the pyridylketone, 4-pyridyl (16), 3-pyridyl (18), or the 2-pyridylketone (20), into contact; for example by mixing together the starting compounds or by dropwise addition of one starting compound to the other. Preferably, the phenylhydrazine is introduced into a vessel and the pyridylketone is added dropwise.

The molar ratio of pyridylketone to phenylhydrazine is generally selected in the range from 0.5:1 to 3:1, especially in the range from 1:1 to 2:1, more especially in the range from 1:1 to 1:1.5.

It is especially advisable to select the reaction temperature for the reaction of the pyridylketone with the phenylhydrazine in the range from 273° to 363° K, especially in the range from 303° to 353° K, more especially in the range from 328° to 253° K.

The reaction pressure chosen is generally in the range from 70 kPa to 10 MPa, especially from 90 kPa to 5 MPa, and is more especially atmospheric pressure.

The duration of the dropwise addition of the pyridylketone to the phenylhydrazine is generally dependent on the reactivity of the starting compounds, on the reaction temperature chosen and on the desired conversion. The duration of the dropwise addition is usually chosen in the range from 2 minutes to two days.

After the addition of the pyridylketone to the phenylhydrazine it is recommended that the reaction mixture obtained be subsequently stirred. The duration chosen for the subsequent stirring is generally from 1 hour to 24 hours.

In addition, the reaction can be carried out with or without solvent, but is preferably carried out in a solvent. Preference is given to organic solvents or solvent mixtures.

Within the context of this invention, solvents are organic solvents and water, or a mixture of organic solvents or a mixture of organic solvents and water.

Organic solvents are, for example, alcohols, for example methanol, ethanol, isopropanol, butanol or glycols, especially isopropanol.

The ratio by weight of phenylhydrazine to the solvent is generally in the range from 20 to 90% by weight, especially in the range from 30 to 60% by weight.

The hydrazon may be advantageously worked up and isolated before being further processed.

Usually, the hydrazon is isolated by filtration and by subsequent drying of the resulting filter cake, which contains the hydrazon.

Filtration is normally carried out in standard filtering equipment, for example Büchner funnels, filter presses, pressurised suction filters, preferably in vacuo.

The temperature for the drying is dependent on the pressure applied. Drying is usually carried out in vacuo at 50–200 mbar.

The drying is usually carried out at a temperature in the range from 313 to 363 K, especially from 323 to 353 K, and more especially in the range from 328 to 348 K.

Then, the intermediate compound, the hydrazon, is reacted with an alkylating or benzylating agent.

The molar ratio of the alkylating or benzylating agent to each reaction centre of the hydrazon is usually in the range from 3:1 to 1:1, especially from 2:1 to 1:1, and more especially from 1.2:1 to 1:1.

After the addition of the alkylating or benzylating agent, adjustment of the pH value of the resulting reaction mixture by means of a base to a pH value in the range from 5 to 8, especially from 6 to 7, is recommended.

The molar ratio of base to alkylating or benzylating agent is generally in the range from 3:1 to 1:1 and especially in the range from 2:1 to 1:1.

Generally, further stirring is then carried out for 30 minutes to 12 hours at from 288 to 333 K.

The chosen reaction pressure is generally atmospheric pressure.

The duration of reaction is generally dependent on the reactivity of the starting compounds, on the reaction temperature chosen and on the desired conversion. The chosen duration of reaction is usually in the range from one hour to, two days, especially in the range from one hour to three hours.

The reaction product obtained can, if desired, be purified and isolated.

In general, the reaction product is usually filtered and then washed with water or a salt solution and subsequently dried.

It has proved advantageous for the product to be purified by recrystallisation after it has been isolated.

Organic solvents and solvent mixtures are suitable for the recrystallisation. Preference is given to alcohols, for example methanol, ethanol, 2-propanol or butanol, especially 2-propanol.

Alkylating agents include, for example, alkyl bromides, alkyl iodides, preferably methyliodide, and alkyl sulfates, for example dimethyl sulfate, diethyl sulfate, dipropyl sulfate or diisopropyl sulfate, and preferably dimethylsulfate.

Benzylating agents include, for example, benzyl halides, such as benzyl bromide and benzyl chloride, especially benzyl chloride, and benzyl halides substituted on the aromatic nucleus; benzyl halides are substituted especially, for example, by hydrogen, $C_1$–$C_8$alkyl, $C_1$–$C_8$alkoxy, cyanide or by halide, more especially by hydrogen.

The dyes of formula (1), (2) or (3) according to the invention are suitable for dyeing organic material, such as keratin, wool, leather, silk, cellulose or polyamides, especially keratin-containing fibres, cotton or nylon, and preferably human hair.

The multiplicity of shades of the dye, which results by the method according to the present invention, can be increased by combination with other dyes.

The present invention relates also to the colouration of hair with a dye of formula (1), (2) or (3) according to the present invention, and at least one further dye.

The dye of formula (1), (2) or (3) of the present invention can be combined with dyes of the same or different class of dyes, especially with direct dyes, oxidation dyes; dye precursor combinations of a coupler compound and a diazotized compound, or a capped diazotized compound; and/or cationic reactive dyes.

Direct dyes are natural or synthetic; they are uncharged, cationic or anionic, such as acid dyes.

Oxidation dye denotes also for oxidation dye precursors, which are from the group of the developer and coupler compounds. Wherein the coupler compounds denotes also to the addition salts thereof with an acid.

In the context of the present invention the single classes of dyes comprise the dyes defined in the Color Index of the Society of Textile Chemist and Colorist.

Further, in the context of the present invention, combinations comprising of a compound of formula (1), (2) or (3) are compositions, formulation and methods.

One preferred embodiment of the present invention is the combination of at least a single compound of formula (1), (2) or (3) with a direct dye, which are described in "Dermatology", edited by Ch. Culnan, H. Maibach, Verlag Marcel Dekker Inc., New York, Basle, 1986, Vol. 7, Ch. Zviak, The Science of Hair Care, chapter 7, pages 248–250, and in "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

More preferred direct dyes for the combination with at least a single compound of formula (1), (2) or (3), especially for semi permanent dyeing, are:

2-Amino-3-nitrophenol, 2-Amino-4-hydroxyethylamino-anisole sulfate, 2-Amino-6-chloro-4-nitrophenol, 2-Chloro-5-nitro-N-hydroxyethylene-p-phenylendiamine, 2-Hydroxyethyl-picramic acid, 2,6-Diamino-3-((pyridine-3yl)-azo)pyridine, 2-Nitro-5-glyceryl-methylaniline, 3-Methylamino-4-nitro-phenoxyethanol, 4-Amino-2-nitrodiphenyleneamine-2'-carboxilic acid, 6-Nitro-1,2,3,4,-tetrahydroquin 4-N-Ethyl-1,4-bis(2'-hydroxyethylamino-2-nitrobenzene hydrochloride, 1-Methyl-3-nitro-4-(2'-hydroxyethyl)-aminobenzene, 3-Nitro-p-hydroxyethyl-aminophenol, 4-Amino-3-nitrophenol, 4-Hydroxypropylamine-3-nitrophenol, Hydroxyanthryl-aminopropylmethyl morphlino methosulfat, 4-Nitrophenyl-aminoethylurea, 6-Nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC Blue 2, HC Blue 7, HC Blue 8, HC Blue 12, HC Orange 1, HC Orange 2, HC Red 1, HC Red 10-11, HC Red 13, HC Red 16, HC Red 3, HC Red BN, HC Red 7, HC Violet 1, HC Violet 2, HC Yellow 2, HC Yellow 5, HC Yellow 5, HC Yellow 6, HC Yellow 7, HC Yellow 9, HC Yellow 12, HC Red 8, Hydroxyethyl-2-nitro-p-toluidine, N,N-Bis-(2-Hydroxyethyl)-2-nitro-p-phenylendiamine, HC Violet BS, Picramic Acid, Solvent Green 7.

More preferred are combinations with cationic azo dyes, for example according to GB-A-2 319 776 as well as the oxazine dyes described in DE-A-299 12 327 and mixtures thereof with the other direct dyes mentioned therein.

Preferred direct dyes for the combination with at least a single compound of formula (1), (2) or (3) or a combination of at least a single compound of formula (1), (2) or (3) and oxidative dyes and oxidization agents, especially for semi permanent dyeing and permanent dyeing, are:

Disperse Violet 4, Picramic acid, N,N'-Bis-(2-Hydroxyethyl)-2-nitro-p-phenylendiamine, HC Yellow No. 5, HC Blue No. 2, HC Yellow No. 2,2-Chloro-5-nitro-N-hydroxyethyl-p-phenylendiamine, HC Red No. 3,4-Amino-3-nitro-phenol, Basic Blue 99, 2-Hydroxyethyl Picramic acid, HC Yellow No. 6, Hydroxyethyl-2-nitro-p-toluidine, 2-Amino-6-chloro-4-nitrophenol, 4-Hydroxypropylamino-3-nitrophenol, Basic Red 2, HC Red No. 16 and HC Blue No. 16.

Further preferred cationic dyes for the combination with a compound of formula (1), (2) or (3) according to the present invention are described in the following references in WO 95/01772, especially on page 2, line 7 to page 4, line 1, and especially on page 4, line 35 to page 8, line 21 and on pages 11 to 27, or in WO 01/66646, especially on page 1, line 18 to page 3, line 16, and preferred from page 16, line 20 to page 22, and cationic dyes as described on pages 10 to 17, or in EP 970 685, especially on page 2, line 44 to page 9, line 56 and preferably on page 9, line 58 to page 48, line 12, or direct dyes are described in DE-A-19 713 698, especially page 2, line 61 to page 3, line 43, or direct dyes and oxidizing agent are described in WO 97/20545, especially on page 1, lines 4 to 10, in particular on page 3, lines 24 to 32, and on page11, line 6 to page 13, line 19, especially with direct dyes are described on page 5, line 28 to page 8, line 20, or cationic dyes and anionic UV-absorbers are described in EP 1 166 752, especially on page 3, line 20 to page 4, line 21, in particular with UV absorber on page 4, lines 26 to 3, and especially on page7, line 47 to page 9, line 56.

More preferred for a combination with a cationic dye of formula (1), (2) or (3) are cationic dyes, such as Basic Yellow 87, Basic Orange 31 or Basic Red 51, or cationic dyes as described in WO 01/66646, especially cationic dye of example 4, or cationic dyes as described in WO 02/31056, especially cationic dye of example 6, compound of formula 106, or cationic dye of formula (3) as described in EP-A-714,954 or a yellow cationic dyes of formula (I)

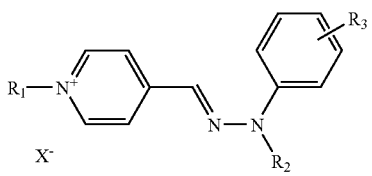

wherein
$R_1$ and $R_2$ are each independently of the other a $C_1$–$C_8$alkyl radical or an unsubstituted or substituted benzyl radical,
$R_3$ is hydrogen, $C_1$–$C_8$alkyl, $C_1$–$C_8$alkoxy, cyanide or halide, preferably hydrogen, and
$X^-$ is an anion, and preferably a compound of formula (I) wherein
$R_1$ is methyl, $R_2$ is benzyl, $R_3$ is hydrogen, and $X^-$ is an anion, or
wherein
$R_1$ is benzyl, $R_2$ is benzyl, $R_3$ is hydrogen, and $X^-$ is an anion, or
wherein
$R_1$ is benzyl, $R_2$ is methyl, $R_3$ is hydrogen, and $X^-$ is an anion, which is defined as given above.

Further preferred for a combination with a cationic dye of formula (1), (2) or (3) are cationic nitroaniline and anthraquinone dyes for the combination a compound of formula (1), (2) or (3) according to the invention, for example those described in the following patent specifications: U.S. Pat. No. 5,298,029, especially in column 2, line 33 to column 5, line 38; U.S. Pat. No. 5,360,930, especially in column 2, line 38 to column 5, line 49; U.S. Pat. No. 5,169,403, especially in column 2, line 30 to column 5, line 38; U.S. Pat. No. 5,256,823, especially in column 4, line 23 to column 5, line 15; U.S. Pat. No. 5,135,543, especially in column 4, line 24 to column 5, line 16; EP-A-818 193, especially on page 2, line 40 to page 3, line 26; U.S. Pat. No. 5,486,629, especially in column 2, line 34 to column 5, line 29; and EP-A-758 547, especially on page 7, line 48 to page 8, line 19.

In addition, preferred are combinations of a compound of formula (1), (2) or (3) according to the invention with further cationic dyes or with other dyes. Preferred are mixtures as given in the below references, with the proviso that one cationic dye is replaced by a compound of formula (1), (2) or (3) according to the present invention.

mixtures of at least two cationic dyes as described in WO 95/01772, especially on page 8, line 34 to page 10, line 22 with the given preferences, or combinations of Pyrazolo-[1,5-a]-pyrimidines with at least one cationic dye as described in EP 998,908, especially on page 2, line 34 to line 42, with preferred Pyrazolo-[1,5-a]-pyrimidines as described in EP 998,908, especially on page 2, line 48 to page 4, line 3, and with preferred cationic direct dyes as described in EP 998,908, especially on page 4, line 22 to page 47, line 24, or combinations of cationic dyes as described in FR-2788432, especially on page 53, line 1 to page 63, line 23, especially a combination of cationic dyes with Arianors in FR-2788432, especially on pages 51 to 52, or especially a combination with at least one Basic Brown 17, Basic brown 16, Basic Red 76 and Basic Red 118, and/or at least one Basic Yellow 57, and/or at least one Basic Blue 99, or combinations of direct dyes and/or an oxidation dye and oxidizing agents in the form of permanent-wave fixing solution, especially with direct dyes as described in DE-A-19 713 698, especially page 4, line 65 to page 35, line 59, or combinations of cationic dyes and an oxidation dye of the developer compound type and oxidizing agents as described in EP 850 638, especially on page 2, line 27 to page 7, line 46 and preferred on page 7, line 20 to page 9, line 26, or combinations of an extemporaneous mixture of a composition (A) containing one or more oxidation dye precursors and optionally one or more couplers, and of a composition (B), in powder form, containing one or more direct dye, preferably cationic, optionally dispersed in an organic pulverulent excipient and/or a mineral pulverulent excipient, and a composition (C) containing one or more oxidizing agent as described in U.S. Pat. No. 6,190,421, especially in column 2, lines 2 to 1, and preferably with oxidation dye precursors as described in column 2, line 35 to column 5, line 13, and preferably with direct dyes as described in column 5, line 30 to column 7, line 14, or a ready-to-use composition comprising, at least one oxidation base, at least one cationic direct dye and at least one enzyme of 2-electron oxidoreductase type in the presence of at least one donor for the said enzyme as described in U.S. Pat. No. 6,228,129, especially in column 26, line 26 to column 27, line 9 with cationic direct dyes as described in column 8, line 17 to column 13, line 65, especially those as described in column 20, line 11 to line 19, in column 23, line 61 to column 24, line 25, or compositions of at least one direct cationic dye and at least one nitrated benzene dye as described in WO 99/20235 on page 2, line 1 to page 7, line 9, and on page 39, line 1 to page 40b line 11, with cationic direct dyes as described on page 8, line 12 to page 25 line 6, and nitro benzene direct dyes as described on page 26, line 7 to page 30, line 15, or compositions of at least one direct cationic dye and at least one autooxidisable oxidation dye, especially benzene, indol and indoline derivatives as described in WO 99/20234, with in preferred direct dyes as given on page 2, line 17 to page 26, line 4, and autooxidisable oxidation dye as described especially on page 26, line 10 to page 28, line 15, or oxidation dyeing compositions of at least one direct dye and at least one meta-Aminophenol derivative and at least one developer compound and an oxidizing agent as described in EP 850 636, especially on page 5, line 41 to page 7, line 52, and preferably on page 19, line 50 to page 22, line 12, with preferred direct dye as described on page 18, lines 1 and 2 in connection with page 7, line 53 to page 17, line 55, and with preferred meta-Aminophenol derivatives as described on page 7, line 47 to line 52, and with preferred developer compounds as described on page 6, line 10 to page 7, line 46, or oxidation dyeing compositions of at least one direct dye and at least one developer compound selected from the group of para-Phenylenediamine derivatives and Bis-Phenylalkylenediamine and, and at least one coupler compound selected from the group of meta-Diphenols and an oxidizing agent, as described in EP-A-850 637, especially on page 6, line 50 to page 8, line 44, oxidation dyeing compositions with cationic couplers, as described in WO 99/48856, especially on page 9, line 16 to page 13, line 8, and page 11, line 20 to page 12, line 13, or cationic dye and e.g. a pyrazolo-(1,5-a)-pyrimidine derivatives, as described in EP 998 908, especially on page 2, line 34 to page 4, line 23, or arianoren and/or oxidative dyes, as described in FR-2 788 432, especially on page 2, line 16 to page 3, line 16, and page 5, line 19 to page 14, line 8, and combinations with cationic dyes as described on page 14, line 23 and following, or oxidative dye precursors (unsaturated aldehyde and coupler compounds), as described in German Patent Application 197 172 24, especially unsaturated aldehydes as described on page 2, line 50 to line 66 and page 3 line 8 to line 12 are used as developer compounds, and primary and secondary amino group compounds, nitrogen-containing heterocyclic compounds, amino acids, oligopeptides, aromatic hydroxy compounds, CH-active compounds as described on page 3, line 42 to page 5 line 25 are used as coupler compounds.

Further preferred for the combination with a compound of formula (1), (2) or (3) are cationic azo dyes, e.g. according to GB-A-2 319 776, as well as the oxazine dyes described in DE-A-29 912 327 and mixtures thereof with the other direct dyes mentioned therein.

More preferred for a combination with a cationic dye of formula (1), (2) or (3) are cationic dyes such as Basic Yellow 87, Basic Orange 31 or Basic Red 51, or as described in WO 01/66646, especially cationic dye of example 4, or as described in WO 02/31056, especially cationic dye of example 6, compound of formula 106.

Especially preferred for a combination with a cationic dye of formula (1), (2) or (3) are direct dye mixtures comprising a dye of formula (1) of WO 01/66646, especially a direct dye of example 4, and/or or a dye of formula (2) of WO 02/31056, especially a direct dye of example 6, and/or Basic Yellow 87, and/or Basic Red 51, and/or Basic Orange 31.

No particular limitation is imposed on the acid dye used in the present invention so far as it is a water-soluble acid dye.

A further embodiment of the present invention concerns the combination of a compound of formula (1), (2) or (3) according to the invention with acid dyes, for example from the group of the compounds known by the international names (Color index), or trade names.

Preferred acid dyes for a combination with a cationic dye of formula (1), (2) or (3) are described in U.S. Pat. No. 6,248,314, they include Red Color No.120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No.104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color No. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401, especially Black Color No. 401, Purple Color 401, Orange Color No. 205.

These acid dyes may be used either single or in any combination thereof.

Preferably they are incorporated in dyeing composition for human hair in a proportion of 0.001–5% by weight (hereinafter indicated merely by "%"), particularly 0.005–4%, more particularly 0.2–3% based on the total weight of the composition, from the viewpoint of practical use in that a sufficient hair-dyeing effect is achieved, and the hand skin is scarcely smeared.

A further embodiment of the present invention concerns the combination of a compound of formula (1), (2) or (3) according to the invention with uncharged dyes, for example from the group of the nitroanilines, nitrophenylenediamines, nitroaminophenols, anthraquinones, indo-phenols, phenazines, phenothiazines, bispyrazolons or bispyrazol aza derivatives or methines.

In addition, the present invention concerns the combination of a compound of formula (1), (2) or (3) according to the invention with oxidation dyes.

Suitable oxidation dyes are described for example in
German Patent Application 19 94 450, especially on page 6, line 6 to line 64, or German Patent Application 19 959 479, especially in column 2, line 6 to column 3, line 11, or in the series "Dermatology", edited by Ch. Culnan, H. Maibach, Verlag Marcel Dekker Inc., New York, Basle, 1986, Vol. 7, Ch. Zviak, The Science of Hair Care, chapter 8, on pages 264–267 (oxidation dyes), or in German Patent Application 19 717 224; unsaturated aldehydes as described on page 2, line 50 to line 66 and on page 3 line 8 to line 12 are used as developer compounds, and primary and secondary amino group compounds, nitrogen-containing heterocyclic compounds, amino acids, oligopeptides, aromatic hydroxy compounds, CH-active compounds as described on page 3, line 42 to page 5 line 8 are used as coupler compounds.

Preferred oxidation dye precursors of the developer type for a combination with a cationic dye of formula (1), (2) or (3) are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives, 2,4,5,6-tetraaminopyrimidin derivatives, or unsaturated aldehydes as described in German Patent Application 19 717 224, especially on page 2, line 50 to line 66 and on page 3 line 8 to line 12, or cationic developer compounds as described in WO 00/43367, especially on page, 2 line 27 to page 8, line 24, in particular on page 9, line 22 to page 11, line 6.

Also very suitable for a combination with a cationic dye of formula (1), (2) or (3) according to the invention are developer dyes in their physiological compatible acid addition salt form, such as hydrochloride or sulfate. Developer dyes, which have aromatic OH substituents are also suitable in their salt form with base, such as alkalimetalphenolates.

Preferred developer compounds are:

1,4-diamino-benzene (p-phenylendiamine), 1,4-diamino-2-methyl-benzene (p-toluylen-diamine), 1,4-diamino-2,6-dimethyl-benzene, 1,4-diamino-2,5-dimethyl-benzene, 1,4-diamino-2,3-dimethyl-benzene, 2-chloro-1,4-diaminobenzene, 4-phenylamino-aniline, 4-dimethylamino-aniline, 4-diethylamino-aniline, hydroxyethyl-p-phenylendiamine, 1-(2'-hydroxyethyl)-2,5- diaminobenzene, N,N-bis-(2-hydroxyethyl)-p-phenylendiamine, 4-[(2-methoxyethyl)amino]-aniline, 4-[(3-hydroxypropyl)amino]-aniline, hydroxypropyl-bis-(N-hydroxyethyl-p-phenylenediamine) hydrochloride, 1,4-diamino-2-(2-hydroxyethyl)-benzene, 1,4-diamino-2-(1-methylethyl)-benzene, 2-(2,5-diaminophenoxy)-ethanol, 1,3-bis[(4-aminophenyl)(2-hydroxyethyl)amino]-2-propanol, bis-(4-hydroxy-5-aminophenyl)-methane, 1,4-bis-(4-aminophenyl)-diazacycloheptane, 1,8-bis(2,5-diaminophenoxy)-3,6-dioxaoctan, 1,10-bis-(2,5-diaminophenyl)-1,4,7, 10-tetraoxadecane, hydroxyethyl-3,4-methylenedioxyaniline, p-aminophenol, o-aminophenol, m-aminophenol, 2-amino-6-methyl-phenol, 4-methylaminophenol sulfate, 4-amino-m-cresol, 6-amino-m-cresol, 6-amino-m-cresol, 2-amino-4-hydroxyethylaminoanisole, 2-amino-5-methyl-phenol, 4-amino-3-methylphenol, 4-methylamino-phenol, 2-aminomethyl-4-aminophenol, 4-amino-2-[(2-hydroxyethyl)-amino]methyl-phenol, 4-amino-2-(2-hydroxyethoxy)-phenol, 4-amino-2-(methoxymethyl)-phenol, 4-amino-2-(2-hydroxyethyl)-phenol, 2-hydroxymethylamino-4-aminophenol, bis-(4-aminophenyl)amine, 4-amino-3-fluorphenol, 2-hydroxymethyl-4-aminophenol, 4-amino-2-(diethylamino)-methyl-phenol, 5-amino-salicylsäure, 2,5-diamino-pyridine, 2-amino-3-hydroxy-pyridine, 2,6-dimethoxy-3,5-diamino-pyridine, 2,4,5, 6-tetraaminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2,5,6-triamino-4-(1H)-pyrimidone, further 4,5-diaminopyrazol derivatives as described in EP 0 740 741 or WO 94/08970, especially 4,5-diamino-1-(2-hydroxyethyl)-1H-pyrazol, 4,5-diamino-1-(1-methylethyl)-1H-pyrazol, 4,5-diamino-1-[(4-methylphenyl)methyl]-1H-pyrazol, 1-[(4-chlorophenyl)methyl]-4,5-diamino-1H-pyrazol, 4,5-diamino-1-methyl-1H-pyrazol.

More preferred developer dyes are p-phenylendiamine, p-toluylendiamine, p-aminophenol, m-aminophenol, o-aminophenol, N,N-bis-(2-hydroxyethyl)-p-phenylendiamine sulfate, 2-amino-4-hydroxyethylaminoanisole sulfate, hydroxyethyl-3,4-methylenedioxyaniline, 1-(2'-hydroxyethyl)-2,5-diaminobenzene, 2,6-dimethoxy-3,5-diamino-pyridine, hydroxypropyl-bis-(N-hydroxyethyl-p-phenylenediamine) hydrochloride, hydroxyethyl-p-phenylendiamine sulfate, 4-amino-3-methylphenol, 4-methylaminophenol sulfate, 2-aminomethyl-4-aminophenol, 4,5-diamino-1-(2-hydroxyethyl)-1H-pyrazol, 4-amino-m-cresol, 6-amino-m-cresol, 5-amino-6-chloro-cresol, 2,4,5,6-tetraaminopyrimidine, 2-hydroxy-4,5,6-triaminopyrimidine, 4-hydroxy-2,5, 6-triaminopyrimidine sulfate.

Preferred oxidation dye precursors of the coupler type for a combination with a cationic dye of formula (1), (2) or (3) are for example m-phenylendiamine derivatives, naphthole, resorcine and resorcine derivatives, pyrazolone and m-aminophenol derivatives.

Especially preferred coupler compounds for a combination with a cationic dye of formula (1), (2) or (3) are N-(3-dimethylamino-phenyl)-urea, 4-amino-2-hydroxytoluene, 2-methyl-5-hydroxyethylaminophenol 2,4-diaminophenoxyethanol, 2-amino-4-[(2-hydroxyethyl)amino]-anisole, p-aminophenol, m-aminophenol and its derivatives, especially 5-amino-2-methylphenol, 5-(3-hydroxypropylamino)-2-methylphenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methyl-phenol, 5-(2'-hydroxyethyl)-amino-2-methylphenol, 3-(diethylamino)-phenol, N-cyclopentyl-3-aminophenol, 1,3-dihydroxy-5-(methylamino)-benzene, 3-(ethylamino)-4-methylphenol and 2,4-dichloro-3-aminophenol, or o-aminophenol and its derivatives, such as 5-methyl-2-(1-methylamino)-phenol, 3-di-methylamino-phenol, 3-diethylamino-phenol, 5-amino-2-methyl-phenol, 5-amino-4-fluor-2-methyl-phenol, 5-amino-4-methoxy-2-methyl-phenol, 5-amino-4-ethoxy-2-methyl-phenol, 3-amino-2, 4-dichlor-phenol, 5-amino-2,4-dichloro-phenol, 3-amino-2-methyl-phenol, 3-amino-2-chloro-6-methyl-phenol, 3-amino-phenol, 2-[(3-hydroxyphenyl)amino]-acetamide, 5-[(2-hydroxyethyl)amino]-2-methyl-phenol, 3-[(2-hydroxyethyl)amino]-phenol, 3-[(2-methoxyethyl)amino]-phenol, 5-amino-2-ethyl-phenol, 2-(4-amino-2-hydroxyphenoxy)-ethanol, 5-[(3-hydroxypropyl)amino]-2-methyl-phenol, 3-[(2,3-dihydroxypropyl)amino]-2-methyl-phenol, 3-[(2-hydroxyethyl)amino]-2-methyl-phenol, m-diaminobenzene and its derivatives such as 2,4-diaminophenoxyethanol, 1,3-bis-(2,4-diaminophenoxy)-propane, 1-methoxy-2-amino-4-(2'-hydroxyethylamino)benzene, 1,3-bis-(2,4-diaminophenyl)-propane, 3-[(2-aminoethyl)amino]-aniline, 1,3-di(2,4-diaminophenoxy)-propane, 1,3-diamino-2,4-dimethoxy-benzene, 2,6-bis(2-hydroxyethyl)amino-toluene, di(2,4-diaminophenoxy)-methane, 3-[di(2-hydroxyethyl)amino]-aniline, 2,6-bis-(2-hydroxyethyl-amino)-1-methylbenzene and 1-amino-3-bis-(2'-hydroxyethyl)-aminobenzene, o-diaminobenzene and its derivatives such as 3,4-diaminobenzoic acid and 2,3-diamino-1-methylbenzene, 2,4-diamino-1-fluor-5-methyl-benzene, 2,4-diamino-1-methoxy-5-methyl-benzene, 1-(2-aminoethoxy)-2,4-diaminobenzene, 2-amino-1-(2-hydroxyethoxy)-4-methylamino-benzene, 2,4-diaminophenoxy-acetic acid, 2,4-diamino-1-ethoxy-5-methyl-benzene, 3-[(2-hydroxyethyl)amino]-aniline, 3,4-diamino-benzoic acid, 3,4-dihydro-6-hydroxy-1,4(2H)-benzoxazine, 6-amino-3,4-dihydro-1,4(2H)-benzoxazine, 2,4-diamino-1,5-di(2-hydroxyethoxy)-benzene, 2,4-diamino-1-(2-hydroxyethoxy)-5-methyl-benzene, 4-amino-2-di[(2-hydroxyethyl)amino]-1-ethoxy-benzene 2,4-di[(2-hydroxyethyl)amino]-1,5-dimethoxy-benzene, 3,4-dihydro-6-hydroxy-1,4(2H)-benzoxazine, 6-amino-3,4-dihydro-1,4(2H)-benzoxazine, di- or trihydroxybenzene derivatives such as resorcine, resorcinmonomethylether, 2-methylresorcine, 5-methylresorcine, 2,5-dimethylresorcine, 1-chloro-2,4-dihydroxy-benzene, 2-chlororesorcine, 4-chlororesorcine, 2,6-dihydroxyethylaminotoluene, 1,2-dichlor-3,5-dihydroxy-4-methyl-benzene, 1,5-dichlor-2,4-dihydroxy-benzene, 1,3-dihydroxy-2-methyl-benzene, pyrogallol and 1,2,4-trihydroxybenzene, pyridine derivatives such as 2,6-diamino-pyridine, 2,6-dihydroxypyridine, 2-amino-3-hydroxypyridine, 2-amino-5-chloro-3-hydroxypyridine, 5-amino-4-chloro-2-methylphenol, 3-diamino-6-methoxy-pyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 2,6-diamino-3,5-dimethoxy-pyridine, and 3,5-diamino-2,6-dimethoxypyridine, naphthaline derivatives such as 1-naphthol, 2-methyl-1-naphthol, 2-hydroxymethyl-1-naphthol, 2-hydroxyethyl-1-naphthol, 1,5-dihydroxynaphthaline, 1,6-dihydroxynaphthaline, 1,7-dihydroxynaphthaline, 1,8-dihydroxynaphthaline, 2,7-dihydroxynaphthaline and 2,3-dihydroxynaphthaline, 2-methyl-i -naphthol-acetat, morpholine derivatives such as 6-hydroxybenzomorpholine and 6-aminobenzomorpholine, chinoxaline derivatives such as 6-methyl-1,2,3,4-tetrahydrochinoxaline, pyrazol derivatives such as -phenyl-3-methylpyrazol-5-one, 3-methyl-1-phenyl-5-pyrazolone, indol derivatives such as 4-hydroxyindol, 5-hydroxy-indol, 6-hydroxyindol and 7-hydroxyindol, 2,3-indolindione, 5,6-dihydroxy-indol, 5,6-dihydroxy-indoline, methylendioxybenzene derivates such as 1-hydroxy-3,4-methylendioxybenzene, 1-amino-3,4-methylendioxybenzene and 1-(2'-hydroxyethyl)-amino-3,4-methylendioxybenzene, 3,4-methylendioxy-phenol, 3,4-methylendioxy-aniline, 5-[(2-hydroxyethyl)amino]-1 ,3-benzodioxol, 6-brom-1-hydroxy-3,4-methylendioxy-benzene, or cationic coupler compounds as described in FR 2 794 644, especially on page 11, line 20 to page 15, line 34, and on page 17, lines 4 to 12, page 178, line 33 to page 18, line 24.

More especially preferred coupler compounds for a combination with a cationic dye of formula (1), (2) or (3) are toluene-2,5-diamine sulfate, 1-naphthol, 1,5-, 2,7- and 1,7-dihydroxynaphthaline, 3-aminophenol, 5-amino-2-methylphenol, 2-amino-3-hydroxypyridine, resorcinol, 4-chlororesorcine, 2-chloro-6-methyl-3-aminophenol, 2,6-dihydroxy-ethylaminotoluene, 2-methyl-5-dihydroxyethylaminophenol, 2,4-diaminophenoxyethylol hydrochloride, 2-methylresorcine, 5-methylresorcine, 2,5-dimethylresorcine, 3,4-methylenedioxyphenol, 2-amino-4-hydroxyethylaminoanisole sulfate, 2,6-di-(beta-hydroxyethylamino)-toluene, 4-amino-2-hydroxytoluene, 6-hydroxyindol, 2-amino-3hydroxypyridine, 2,6-dimethoxy-3,5-pyridinediamine hydrochloride and 2,6-dihydroxy-3,4-dimethylpyridine.

Most preferred coupler compounds for a combination with a cationic dye of formula (1), (2) or (3) are 2-chloro-6-methyl-3-aminophenol, 5-amino-2-methylphenol, 2-amino-3-hydroxypyridine, 2,6-di-(beta-hydroxyethylamino)-toluol, 2-methylresorcine and 1-naphthol.

Further, preferred for a combination with a cationic dye of formula (1), (2) or (3) are:
the developer/-coupler combination 2,4,5,6-Tetraaminopyrimidine and 2-Methylresorcine are preferred for assessing of red shades, or
p-Toluenediamine and 4-Amino-2-hydroxytoluene for assessing of blue-violet shades, or
p-Toluenediamine and 2-Amino-4-hydroxyethylaminoanisole for assessing of blue shades, or
p-Toluenediamine and 2,4-Diamino-phenoxyethynol for assessing of blue shades, or
3-Methyl-4-aminophenol and 4-Amino-2-hydroxytlouene for assessing of orange shades, or
p-Toluenediamine and resorcine for assessing of brown-green shades, or
p-Toluenediamine and 1-Naphthol for assessing of blue-violet shades, or
p-Toluenediamine and 2-methylresorcine for assessing of brown-gold shades.

Further, one preferred embodiment of the present invention concerns the combination of a compound of formula (1), (2) or (3) according to the present invention with autooxidizable compounds, such as, for example benzene, indol, or indoline, especially 5,6-dihydroxyindol or 5,6-dihydroxyindoline derivatives as described in WO 99/20234, especially on page 26, line 10 to page 28, line 15, or in WO 00/28957 on page 2, third paragraph.

Preferred autooxidizable benzene derivatives for a combination with a cationic dye of formula (1), (2) or (3) are: 1,2,4-trihydroxybenzene, 1-methyl-2,4,5-trihydroxybenzene, 2,4-diamnio-6-methylphenol, 2-amino-4-methylaminophenol, 2,5-diamino-4-methyl-phenol, 2,6-diamino-4-diethylaminophenol, 2,6-diamino-1,4-dihydroxybenzen, and the salts of these compounds, which are accessible with acid.

Preferred autooxidizable indol derivatives for a combination with a cationic dye of formula (1), (2) or (3) are:
5,6-dihydroxyindol, 2-methyl-5,6-dihydroxyindol, 3-methyl-5,6-dihydroxyindole, 1-methyl-5,6-dihydroxyindol, 2,3-dimethyl-5,6-dihydroxyindol, 5-methoxy-6-dihydroxyindol, 5-acetoxy-6-hydroixyindol, 5,6-diacetoxyindol, acid of 5,6-dihydroxyindol-2-carbonacid, and the salts of these compounds, which are accessible with acid.

Preferred autooxidizable indoline derivatives for a combination with a cationic dye of formula (1), (2) or (3) are:
5,6-dihydroxyindoline, 1-methyl-5,6-dihydroxyindoline, 1-ethyl-5,6-dihydroxyindoline, and the salts of these compounds, which are accessible with acid.

A compound of formula (1), (2) or (3) according to the present invention can also be combined with at least two different developers and at least one coupler compound, or with at least two different couplers and at least one developer compound. Such combinations are for example described in German Patent Application 197 172 24, especially on page 3, line 31 to page 5, line 8.

In addition, a compound of formula (1), (2) or (3) according to the present invention may also be combined with naturally occurring dyes, such as, for example, henna red, henna neutral, henna black, camomile blossom, sandalwood, black tea, Rhamnus frangula bark, sage, campeche wood, madder root, catechu, sedre and alkanet root. Such colouring methods are described, for example, in EP-A-404 868, especially on page 3, line 55 to page 4, line 9.

Further, a compound of formula (1), (2) or (3) may also be combined with capped diazotised compounds.

Capped diazonium compounds that come into consideration include, for example, antidiazotates of formula

(22)

diazosulfonates of formula

(23)

triazenes of formula

(24)

and also cyclic triazenes of formula

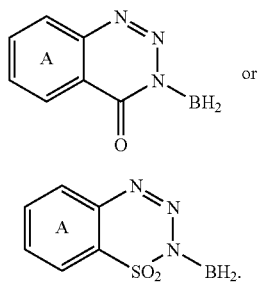

(24)

(25)

In formula (22) to (25):

A is the radical of an unsubstituted or substituted, aromatic or heterocyclic aryl, B is the radical of an unsubstituted or substituted, water-soluble, aliphatic or aromatic aryl and R is an unsubstituted or substituted alkyl group, it being necessary for at least one of the groups to contain a water-solubilising radical.

As a water-solubilising radical there comes into consideration, for example, $SO_3H$, COOH, OH or a quaternised ammonium radical of formula

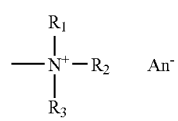

(26)

wherein $R_1$, $R_2$ and $R_3$ are each independently of the others unsubstituted or substituted alkyl and An is an anion.

According to the invention, alkyl groups R, $R_1$, $R_2$ and $R_3$ are to be understood generally as open-chain or branched alkyl radicals, for example methyl, ethyl, n- and iso-propyl or n-, sec- and tert-butyl.

Such alkyl radicals may be mono- or poly-substituted, for example by hydroxy, carboxy, halogen, cyano or $C_1$–$C_4$alkoxy.

Preferably, the alkyl groups are unsubstituted and each has from 1 to 4, especially 1 or 2, carbon atoms.

As anion An there come into consideration both inorganic and organic anions, for example halide, such as chloride, bromide or iodide, sulfate, hydrogen sulfate, methyl sulfate, formate, acetate or lactate.

The anion is generally governed by the preparation process. Preferably, it is chloride, hydrogen sulfate, sulfate, methosulfate or acetate.

A is the radical of an unsubstituted or substituted, aromatic or heterocyclic aryl. Suitable radicals include, for example, unsubstituted or substituted radicals of benzene, radicals at position 1- or 2- of naphthalene, radical at position 2- of thiophene, radical at position 2- of 1,3-thiazole, radical at position 5- of 1,2-thiazole, radical at position 2- of 1,3-benzothiazole, radical at position 1- of 2,3-benzothiazole, radical at position 2- of aminoimidazole, radical at position 2- of 1,3,4-thiadiazole, radical at position 2- of 1,3,5-thiadiazole, radical at position 2- of 1,3,4-triazole, radical at positions 3-, 7- or 8- of pyrazole, radical at position 2- of benzimidazole, radical at position 2- of benzopyrazole, radical at positions 2- or 4- of pyridine, radical at positions 2-, 3-, 4-, 7- or 8- of quinoline, radical at position 2- of aminopyrimidine and radical at position 3- of aminoisoxazole, radical at position 5- of aminoquinoline, radical at position 4- of aminodiphenylamine, radical at position 2- of aminodiphenyl ether and radical at position 4- of aminoazobenzene.

Such radicals may be mono- or poly-substituted, for example by $C_1$–$C_4$alkyl, $C_1$–$C_4$alkoxy, $C_1$–$C_4$alkylthio, halogen, for example fluorine, bromine or chlorine, nitro, trifluoromethyl, CN, SCN, $C_1$–$C_4$alkylsulfonyl, phenylsulfonyl, benzylsulfonyl, di-$C_1$–$C_4$alkylaminosulfonyl, $C_1$–$C_4$alkylcarbonylamino, $C_1$–$C_4$alkoxysulfonyl or by dihydroxy-$C_1$–$C_4$alkylaminosulfonyl.

B is the radical of an unsubstituted or substituted, water-soluble, aliphatic or aromatic aryl, suitable aliphatic aryls including especially those carrying a carboxylic acid or sulfonic acid group, for example starting materials for B radicals are: methylaminoacetic acid (sarcosine), methylaminobutyric acid, methylaminopropionic acid, ethylaminoacetic acid, ethylaminobutyric acid, 1-methylaminoethane-2-sulfonic acid, 1-ethylaminoethane-2-sulfonic acid and 1-methylaminopropane-3-sulfonic acid.

As starting materials for B radicals come into consideration especially aniline compounds and aminonaphthalene compounds, especially those carrying a carboxylic acid or sulfonic acid group. The amino group of such compounds may be unsubstituted but is preferably substituted, for example by unsubstituted or substituted $C_1$–$C_4$alkyl, suitable substituents thereof being especially hydroxy or carboxy.

Suitable coupling components include, for example, the coupling components customarily used for azo dyes and known from the relevant literature, for example those of the benzene series, the naphthalene series, the open-chain methylene-active compounds (for example acylacetarylamides) and the heterocyclic series.

The compounds of formula (22), (23), (24) and (25) are known, or can be prepared in a manner known per se.

The compounds of formula (23) wherein B is the radical of an aliphatic aryl are likewise known or can be prepared in a manner known per se.

The compounds of formula (27)

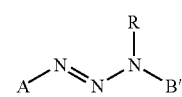

(27)

wherein

A is the radical of an unsubstituted or substituted, water-soluble, aromatic or heterocyclic aryl, B' is the radical of an unsubstituted or substituted, water-soluble, aliphatic or aromatic aryl, and R is an unsubstituted or substituted alkyl group, can likewise be prepared in a manner known per se.

For A and R, the definitions and preferred meanings indicated for formula (22) to (25) apply and, for B', the definitions and preferred meanings indicated for B in formula (22) to (25) apply in so far as they relate to aromatic amines.

The compounds of formula (27) can be prepared, for example, by diazotising an amine of formula A—$NH_2$ in customary manner and coupling it to an amine of formula B'—NHR, there coming into consideration as amines B'—NHR only those compounds which couple at the nitrogen atom and not at a carbon atom of the aromatic ring. Such compounds are preferably aniline derivatives substituted in the 4 positions.

The present invention also describes formulations, which are used for the colouration of keratin fibres, especially human hair.

The formulations are applicable on human hair in different technical forms. The specific technical form may be chosen in view of the envisaged application and/or dye or dye composition. Technical forms of formulation are for example a solution, especially a thickened watery or watery alcoholic solution, a cream, foam, shampoo, powder, a gel, or an emulsion.

Preferred forms of formulations are ready to use compositions or a multi-compartment dyeing device or 'kit' or any of the multi-compartment packaging systems with compartments as described for example as described in U.S. Pat. No. 6,190,421, column 2, lines 16 to 31.

It is of advantage to prepare compositions of dyes, which are not stable to reduction, with oxidizing agent free compositions just before the dyeing process.

One preferred embodiment of the present invention concerns the formulation of dyes, especially those of formula (1), (2) or (3) in powder form.

The colouring compositions according to the invention may furthermore comprise any active ingredient, additive or adjuvant known for such preparations.

Adjuvants that are suitable for such formulations are in general customary in the field hair-colouring, such as for example surfactants or tensides, solvents, bases, acids, perfumes, polymeric adjuvant, thickeners and light stabilisers.

Preferred combinations of the colouring compositions according to the invention with adjuvant used in the colouring of hair, are combination of direct dyes with oxidizing agents to achieve lightened colouration; wherein oxidizing agents especially described in WO 97/20545, especially page 9, lines 5 to 9, combination of direct dyes and/or an oxidation dye and oxidizing agents in the form of permanent-wave fixing solution, especially oxidizing agents as described in DE-A-19 713 698, especially page 4, lines 52 to 55, or EP-A-1 062 940, especially page 6, lines 41 to 47, (and in the equivalent WO 99/40895), oxidation dyes in the presence of oxidoreductase enzyme, as described in WO 99/17730, especially page 4, line 11 to page 13, line 28, and WO 99/36034, especially pages 3 to 15, combination of cationic dyes with polyols or polyethers; polyols or polyethers as described in EP-A-962 219, especially page 27, lines 14 to 38, thickening polymers, as described in EP-A-970 684, especially page 48, line 16 to page 51, line 4, sugar-containing polymers, as described in EP-A-970 687, especially page 28, line 17 to page 29, line 23, quaternary ammonium salts, as described in WO 00/10517, especially page 44, line 16 to page 46, line 23, anionic surfactants, as described in WO 00/10518, especially page 45, line 11 to page 48, line 3, non-ionic surfactants, as described in WO 00/10519, especially page 45, line 11 to page 50, line 12, or silicones, as described in WO 00/12057, especially page 45, line 9 to page 55, line 2.

oxidative agent or laser and direct dyes, as described in EP-920 856, especially on page 2, line 31 to page 53 line 36, and on page 49, line 38 to page 50, line 41, with direct dyes as described on page 3, line 54 to page 48, line 52, or direct dyes in the presence of cationic amphotere, substantive polymer, as described in EP-953 334, especially on page 2, line 39 to page 7, line 44, with direct dyes as described on page 8, line 54 to page 27, line 16, and polymers as described on page 27, line 17 to page 30, line 14, or direct dyes formulations with polymer thickener on the basis of acrylic acid, as described in EP-970 685, especially on page 2, line 39 to page 10, line 1, with direct dyes as described on page 10, line 7 to page 48, line 15, with polymers as described on page 48, line 17 to page 49, line 28.

The colouring composition according to the invention in many cases comprises at least one surfactant. Suitable surfactants are anionic, zwitterionic, ampholytic, non-ionic and cationic surfactants. In many cases, however, it has proved advantageous to select the surfactants from anionic, zwitterionic and non-ionic surfactants.

Anionic surfactants suitable for use in the colouring compositions according to the invention include all anionic surface-active substances that are suitable for use on the human body. Such substances are characterised by an anionic group that imparts water solubility, for example a carboxylate, sulfate, sulfonate or phosphate group, and a lipophilic alkyl group having approximately from 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:

linear fatty acids having from 10 to 22 carbon atoms (soaps), ether carboxylic acids of formula R—O—(CH$_2$—CH$_2$—O)$_x$—CH$_2$—COOH, in which R is a linear alkyl group having from 10 to 22 carbon atoms and x=0 or from 1 to 16, acyl sarcosides having from 10 to 18 carbon atoms in the acyl group, acyl taurides having from 10 to 18 carbon atoms in the acyl group, acyl isothionates having from 10 to 18 carbon atoms in the acyl group, sulfosuccinic mono- and di-alkyl esters having from 8 to 18 carbon atoms in the alkyl group and sulfosuccinic monoalkylpolyoxyethyl esters having from 8 to 18 carbon atoms in the alkyl group and from 1 to 6 oxyethyl groups, linear alkane sulfonates having from 12 to 18 carbon atoms, linear α-olefin sulfonates having from 12 to 18 carbon atoms, α-sulfo fatty acid methyl esters of fatty acids having from 12 to 18 carbon atoms, alkyl sulfates and alkyl polyglycol ether sulfates of formula R'—O(CH$_2$—CH$_2$—O)$_x$—SO$_3$H, in which R' is a preferably linear alkyl group having from 10 to 18 carbon atoms and x'=0 or from 1 to 12, mixtures of surface-active hydroxysulfonates according to DE-A-3 725 030, especially page 3, lines 40 to 55, sulfated hydroxyalkylpolyethylene and/or hydroxyalkylenepropylene glycol ethers according to DE-A-3 723 354, especially page 4, lines 42 to 62, sulfonates of unsaturated fatty acids having from 12 to 24 carbon atoms and from 1 to 6 double bonds according to DE-A-3 926 344, especially page 2, lines 36 to 54, esters of tartaric acid and citric acid with alcohols which are addition products of approximately from 2 to 15 molecules of ethylene oxide and/or propylene oxide with fatty alcohols having from 8 to 22 carbon atoms, or anionic surfactants, as described in WO 00/10518, especially page 45, line 11 to page 48, line 3.

Preferred anionic surfactants are alkyl sulfates, alkyl polyglycol ether sulfates and ether carboxylic acids having from 10 to 18 carbon atoms in the alkyl group and up to 12 glycol ether groups in the molecule, and also especially salts of saturated and especially unsaturated $C_8$–$C_{22}$carboxylic acids, such as oleic acid, stearic acid, isostearic acid and palmitic acid.

Surface-active compounds that carry at least one quaternary ammonium group and at least one —COO$^{(-)}$ or —SO$_3^{(-)}$ group in the molecule are termed zwitterionic surfactants. Zwitterionic surfactants that are especially suitable are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocoamidopropyl betaine.

Ampholytic surfactants are to be understood as meaning surface-active compounds that, in addition to a $C_8$–$C_{18}$-alkyl or -acyl group, contain at least one free amino group and at least one —COOH or —SO$_3$H group in the molecule and are capable of forming internal salts.

Examples of suitable ampholytic surfactants include N-alkylglycines, N-alkylpropionic acids, N-alkylaminobutyric acids, N-alkyliminodipropionic acids, N-hydroxyethyl-N-alkylamidopropyl-glycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkyl-aminopropionate, cocoacylaminoethylaminopropionate and $C_{12}$–$C_{18}$acylsarcosine.

Non-ionic surfactants are described in WO 00/10519, especially page 45, line 11 to page 50, line 12.

Non-ionic surfactants contain as the hydrophilic group, for example, a polyol group, a polyalkylene glycol ether group or a combination of polyol and polyglycol ether groups.

Such compounds are, for example:
addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, $C_{12}$–$C_{22}$ fatty acid mono- and di-esters of addition products of from 1 to 30 mol of ethylene oxide with glycerol, $C_8$–$C_{22}$alkyl-mono- and -oligo-glycosides and ethoxylated analogues thereof, addition products of from 5 to 60 mol of ethylene oxide with castor oil and hydrogenated castor oil, addition products of ethylene oxide with sorbitan fatty acid esters, addition products of ethylene oxide with fatty acid alkanolamides.

Examples of cationic surfactants that can be used in the colouring compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyldimethy-lammonium chloride, lauryldimethylammonium chloride, lauryldimethylbenzylammonium chloride and tricetylmethylammonium chloride. Further cationic surfactants that can be used in accordance with the invention are quaternised protein hydrolysates.

Also suitable in accordance with the invention are cationic silicone oils, such as, for example, the commercially available products Q2-7224 (manufacturer: Dow Coming; a stabilised trimethylsilylamodimethicone), Dow Coming 929 emulsion (comprising a hydroxyamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80), or silicones, as described in WO 00/12057, especially page 45, line 9 to page 55, line 2.

Alkylamidoamines, especially fatty acid amidoamines, such as the stearylamidopropyl-dimethylamine obtainable under the name Tego Amid® 18, are distinguished not only by a good conditioning action but also especially by their good biodegradability.

Quaternary ester compounds, so-called "esterquats", such as the methyl hydroxyalkyl-dialkoyloxyalkylammonium methosulfates marketed under the trademark Stepantex®, are also very readily biodegradable.

An example of a quaternary sugar derivative that can be used as cationic surfactant is the commercial product Glucquat® 100, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

The surfactants that are addition products of ethylene and/or propylene oxide with fatty alcohols or derivatives of such addition products may either be products having a "normal" homologue distribution or products having a restricted homologue distribution. "Normal" homologue distribution is to be understood as meaning mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts. The use of products having restricted homologue distribution may be preferred.

Further preferred active ingredients of formulation according to the present invention, adjuvants and additives are as follows:

non-ionic polymers, for example vinylpyrrolidone/vinyl acrylate copolymers, polyvinyl-pyrrolidone and vinylpyrrolidone/vinyl acetate copolymers and polysiloxanes, cationic polymers, such as quaternised cellulose ethers, polysiloxanes having quaternary groups, dimethyldiallylammonium chloride polymers, copolymers of dimethyldiallyl-ammonium chloride and acrylic acid, as available commercially under the name Merquat® 280 and the use of which in hair colouring is described, for example, in DE-A-4 421 031, especially page 2, lines 20 to 49, or EP-A-953 334, especially page 27, line 17 to page 30, line 11, acrylamide/dimethyldiallylammonium chloride copolymers, diethyl-sulfate-quaternised dimethylaminoethyl methacrylate/vinylpyrrolidone copolymers, vinylpyrrolidone/imidazolinium methochloride copolymers, quaternised polyvinyl alcohol, zwitterionic and amphoteric polymers, such as, for example, acrylamido-propyl-trimethylammonium chloride/acrylate copolymers and octylacrylamide/methyl methacrylate/tert-butylaminoethyl methacrylate/2-hydroxypropyl methacrylate copolymers, anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers, thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol, structuring agents, such as glucose and maleic acid, hair-conditioning compounds, such as phospholipids, for example soya lecithin, egg lecithin, and cephalins, silicone oils, and also conditioning compounds, for example such as those described in DE-A-19 729 080, especially page 2, lines 20 to 49, EP-A-834 303, especially page 2, line 18 to page 3, line 2, or EP-A-312 343, especially page 2, line 59 to page 3, line 11, protein hydrolysates, especially elastin, collagen, keratin, milk protein, soya protein and wheat protein hydrolysates, condensation products thereof with fatty acids and also quaternised protein hydrolysates, perfume oils, dimethyl isosorbitol and cyclodextrins, solubilisers, such as ethanol, isopropanol, ethylene glycol, propylene glycol, glycerol and diethylene glycol, anti-dandruff active ingredients, such as piroctones, olamines and zinc Omadine, further substances for adjusting the pH value, active ingredients such as panthenol, pantothenic acid, allantoin, pyrrolidonecarboxylic acids and salts thereof, plant extracts and vitamins, cholesterol, light stabilisers and UV absorbers, as described, for example, in EP-A-819 422, especially page 4, lines 34 to 37, consistency regulators, such as sugar esters, polyol esters or polyol alkyl ethers, fats and waxes, such as spermaceti, beeswax, montan wax, paraffins, fatty alcohols and fatty acid esters, fatty alkanolamides, polyethylene glycols and polypropylene glycols having a molecular weight of from 150 to 50 000, for example such as those described in EP-A-801 942, especially page 3, lines 44 to 55, complexing agents, such as EDTA, NTA and phosphonic acids, swelling and penetration substances, such as polyols and polyol ethers, as listed extensively, for example, in EP-A-962 219, especially page 27, lines 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole, opacifiers, such as latex, pearlising agents, such as ethylene glycol mono- and di-stearate, propellants, such as propane-butane mixtures, $N_2O$, dimethyl ether, $CO_2$ and air, and also antioxidants, polyols or polyethers, as described in EP-A-962 219, especially page 27, lines 14 to 38, thickening polymers, as described in EP-A-970 684, especially page 48, line 16 to page 51, line 4, sugar-containing polymers, as described in EP-A-970 687, especially page 28, line 17 to page 29, line 23, quaternary ammonium salts, as described in WO 00/10517, especially page 44, line 16 to page 46, line 23.

In the context of the present invention, oxidizing agents are understood to be any oxidizing agent customarily used for oxidative hair colouring, for example dilute hydrogen peroxide solutions, hydrogen peroxide emulsions or hydrogen peroxide gels, alkaline earth metal peroxides, organic peroxides, such as urea peroxides, melamine peroxides, or alkalimetalbromat fixations are also applicable if a shading powder on the basis of semi-permanent, direct hair dyes is used.

Preferred oxidizing agent is hydrogen peroxide, preferred in about 2 to 30% by weight, more preferred in 3 to 20% by weight, and most preferred in 6 to 12% by weight of the total weight of a watery composition such as a solution, dispersion, a gel or emulsion.

The watery composition can comprise all customary components, which are used for the different applications of oxidizing agent compositions as described in K. Schrader, "Grundlagen und Rezepturen der Kosmetika", 2. Aufl. (1989), page 832–840.

Further preferred oxidizing agents are oxidizing agents to achieve lightened colouration, as described in WO 97/20545, especially page 9, lines 5 to 9, oxidizing agents in the form of permanent-wave fixing solution, as described in DE-A-19 713 698, especially page 4, lines 52 to 55, and lines 60 and 61 or EP-A-1 062 940, especially page 6, lines 41 to 47, (and in the equivalent WO 99/40895).

An oxidizing agents may be present in the colouring compositions according to the invention preferably in an amount of from 0.01% to 6%, especially from 0.01% to 1%, based on the total dyeing composition.

Preferred catalysts are metal ions, such as for example $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$, preferably $Zn^{2+}$, $Cu^{2+}$ and $Mn^{2+}$.

The metal ions are applicable in any physiological suitable salts form. Preferred salts are acetate, sulfate, halogenide, lactate and tartrate.

Alkalimetalsulfits, such as sodium-, potassium-, lithium-sulfite, Alkalimetaldisulfits, such as sodium-, potassium-, lithium-disulfite, ascorbic acid, tert.-Butylhydrochinon and Ammoniumthiolactat.

In general, the coloration with an oxidative agent is conducted in the presence of a base. Bases are for example ammonia, alkali metal carbonates, earth metal carbonates, alkanol amines, such as for example mono-, di- or triethanolamine, alkali metal hydroxides, earth metal hydroxides, compounds of the formula

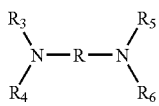

wherein,

R is a propyl residue, which substituted with OH or $C_1$–$C_4$-alkyl, $R_3$, $R_4$, $R_5$ and $R_6$ are independently or dependently from each other hydrogen, $C_1$–$C_4$-alkyl or hydroxy-($C_1$–$C_4$)-alkyl.

Alkali metal is for example sodium, potassium or lithium.

Earth metal is for example magnesium or calcium.

Acids are inorganic or organic acids, such as hydrochloride, tartrat acid, citric acid, ascorbic acid and phosphor acid.

The use of UV absorbers can effectively protect natural and dyed hair from the damaging rays of the sun and increase the wash fastness of dyed hair.

Preferred UV absorbers the colouring compositions according to the invention are:
  cationic benzotriazole UV absorbers as for example described in WO 01/36396 especially on page 1, line 20 to page 2, line 24, and preferred on page 3 to 5, and on pages 26 to 37, or
  cationic benzotriazole UV in combination with antioxidants as described in WO 01/36396, especially on page 11, line 14 to page 18, or
  UV absorbers in combination with antioxidants as described in U.S. Pat. No. 5,922,310, especially in column 2, lines 1 to 3,
  UV absorbers in combination with antioxidants as described in U.S. Pat. No. 4,786,493, especially in column 1, 42 to column 2, line 7, and preferred in column 3, 43 to column 5, line 20, or
  combination of UV absorbers as described in U.S. Pat. No. 5,830,441, especially in column 4, lines 53 to 56, or
  combination of UV absorbers as described in WO 01/36396, especially on page 11, lines 9 to 13, or
  triazine derivatives provide effective UV protection as described in WO 98/22447, especially on page 1, line 23 to page 2, line 4, and preferred on page 2, line 11 to page 3, line 15 and most preferred on pages 6 to 7, and 12 to 16, or
  combination of the cosmetic formulations as described in WO 98/22447 with one or more than one further UV filter as described in the following patents:

| | |
|---|---|
| EP 895776 | Comp. in Rows 48–58, p 3; R 25 + 33, p 5 |
| WO 9220690 | Polymeric comp in Examples 3–6 |
| EP 1000950 | Comp. in Table 1, pp 18–21 |
| EP 1060734 | T 1–3, pp 11–14 |
| EP 1059082 | Ex 1; T 1, pp 9–11 |
| EP 1008586 | Ex 1–3, pp 13–15 |
| EP 1005855 | T 3, p 13 |
| EP 1129695 | Ex 1–7, pp 13–14 |
| EP 967200 | Ex 2; T 3–5, pp 17–20 |
| EP 945125 | T 3 a + b, pp 14–15 |
| EP 924246 | T 2, p 9 |
| EP 911020 | T 2, p 11–12 |
| EP 916335 | T 2–4, pp 19–41 |
| EP 852137 | T 2, pp 41–46 |
| EP 858318 | T 1, p 6 |
| EP 826361 | T 1, pp 5–6 |
| EP 503338 | T 1, pp 9–10 |
| WO 9301164 | T 1 + 2, pp 13–22 |
| EP 823418 | Ex 1–4, pp 7–8 |
| WO 9714680 | Ex 1–3, p 10 |
| EP 1027883 | Compound VII, p 3 |
| EP 832641 | Ex 5 + 6 p 7; t 2, p 8 |
| U.S. Pat. No. 5,338,539 | Ex 1–9, pp 3 + 4 |
| EP 517103 | Ex 3, 4, 9, 10 pp 6–7 |
| EP 1123934 | T 3, p 10 |
| EP 1027883 | Comp I–VI, p 3 |
| EP 969004 | Ex 5, T 1, pp 6–8 |
| U.S. Pat. No. 5,801,244 | Ex 1–5, pp 6–7 |
| EP 832642 | Ex 22, T 3 pp, 10–15; T 4, p 16 |
| U.S. Pat. No. 5,346,691 | Ex 40, p 7; T 5, p 8 |
| EP 570838) | |
| EP 517104 | Ex 1, T 1, pp 4–5; Ex 8, T 2, pp 6–8 |
| WO 200149686 | Ex 1–5, pp 16–21 |
| EP 944624 | Ex 1 + 2, pp 13–15 |
| EP 933376 | Ex 1–15, pp 10–21 |
| EP 863145 | Ex 1–11, pp 12–18 |
| EP 780382 | Ex 1–11, pp 5–7 |
| EP 626950 | All examples |
| EP 1081140 | Ex 1–9, pp 11–16 |
| WO 9217461 | Ex 1–22, pp 10–20 |
| WO 0168047 | Tables on pp 85–96 |
| EP 613893 | Ex 1–5 + 15, T 1, pp 6–8 |
| EP 1064922 | Compounds 1–34, pp 6–14 |
| EP 1028120 | Ex 1–5, pp 5–13 |
| EP 1008593 | Ex 1–8, pp 4–5 |
| EP 669323 | Ex 1–3, p 5 |
| EP 1108712 | 4,5-Dimorpholino-3-hydroxypyridazine |
| JP 2000319629 | CAS Regno. 80142-49-0, 137215-83-9, 307947-82-6 |
| EP 420707 B1 | Ex 3, p 13 (80142-49-0) |
| U.S. Pat. No. 5,635,343 | All examples |
| EP 1167358 | All examples |

(Abbreviations T: table, R: row, Comp: compound, Ex: compound(s) of patent example, p = page; pp = pages)

A preferred embodiment of the present invention concerns the combination of a compound of formula (1), (2) or (3) with UV absorbers.

Preferred UV absorbers are described in WO 98/22447.

Preferred cosmetic formulations contain a combination of a compound of formula (1), (2) or (3) with UV absorbers and one or more than one further UV protective of the following substance classes:

p-aminobenzoic acid derivatives, for example 4-dimethylaminobenzoic acid 2-ethylhexyl ester;

salicylic acid derivatives, for example salicylic acid 2-ethylhexyl ester;

benzophenone derivatives, for example 2-hydroxy-4-methoxybenzophenone and its 5-sulfonic acid derivative;

dibenzoylmethane derivatives, for example 1-(4-tert-butylphenyl)-3-(4-methoxyphenyl)-propane-1,3-dione;

diphenylacrylates, for example 2-ethylhexyl 2-cyano-3,3-diphenylacrylate, and 3-(benzofuranyl) 2-cyanoacrylate;

3-imidazol-4-ylacrylic acid and esters;

benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;

polymeric UV absorbers, for example the benzylidene malonate derivatives described in EP-A-709 080;

cinnamic acid derivatives, for example the 4-methoxycinnamic acid 2-ethylhexyl ester and isoamyl ester or cinnamic acid derivatives described in U.S. Pat. No. 5,601,811 and WO 97/00851; camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;

hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrsilyl-2''-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;

benzotriazole compounds, for example 2,2'-methylene-bis(6-(2H-benzotriazol-2-yl)-4-(1,1,3,3-tetramethylbutyl)-phenol;

trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;

2-phenylbenzimidazole-5-sulfonic acid and salts thereof;

methyl o-aminobenzoates;

physical sunscreens coated or not as titanium dioxide, zinc oxide, iron oxides, mica, MnO, $Fe_2O_3$, $Ce_2O_3$, $Al_2O_3$, $ZrO_2$. (surface coatings: polymethylmethacrylate, methicone (methylhydrogenpolysiloxane CAS 9004-73-3), dimethicone, isopropyl titanium triisostearate (CAS 61417-49-0), metal soaps as magnesium stearate (CAS 4086-70-8), perfluoroalcohol phosphate as C9-15 fluoro-alcohol phosphate (CAS 74499-44-8; JP 5-86984, JP 4-330007)). The primary particle size is an average of 15 nm–35 nm and the particle size in dispersion is in the range of 100 nm–300 nm.

aminohydroxy-benzophenone derivatives disclosed in DE 10011317, EP 1133980 and EP 1046391 phenyl-benzimidazole derivatives as disclosed in EP 1167358

The UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

Synergistic effects are observed when UV absorbers are used in combination with antioxidants. Examples of antioxidants that can be used are listened in WO 01/36396 (pages 11–18), U.S. Pat. No. 5,922,310 and U.S. Pat. No. 4,786,493.

Further preferred UV absorbers used in addition to the uncharged and cationic benzotriazole UV absorbers in the formulations without limitation to those listed in the following are benzophenone-type substances such as benzophenone-1, benzophenone-2, benzophenone-3, benzophenone-4, benzophenone-5 (sodium salt) or benzotriazol-type substances such as benzenesulfonic acid, 3-(2H-benzotriazol-2-yl)-4-hydroxy-5-(1-methylpropyl)-, monosodium salt; 2-(5-chloro-2H-benzotriazol-2-yl)-6-(1,1-dimethylethyl)-4-methyl-phenol; 2-(2H-benzotriazol-2-yl)-6-dodecyl-4-methyl-phenol, branched and linear. Typical ingredients in the oil phase of emulsions (water in oil, oil in water or triple emulsion) or used in hair oils can be chosen from the following substance groups without limiting the kind of lipophilic ingredients to those substances:

Suitable cosmetic preparations may contain usually from 0.05 to 40% by weight, preferably from 0.1 to 20% by weight, based on the total weight of the composition, of one or more UV absorbers.

Preferred are the cosmetic preparations contain at least one triazine derivative UV absorber, for example, from 0.1 to 40% by weight, preferably from 0.1 to 20% by weight and especially from 0.5 to 10% by weight, based on the total weight of the composition, and the cosmetic preparations contain at least one cationic benzotriazole from 0.05–20% by weight, preferred from 0.1–20% by weight, based on the total weight of the composition. Typical cosmetic formulations containing uncharged and/or cationic benzotriazoles and/or antioxidants alone or in combinations are rinse-off products (e.g. shampoos, hair rinses, conditioners etc.), Suitable cosmetic formulations are:

cosmetic hair-treatment preparations, e.g. hair-washing preparations in the form of shampoos and conditioners, hair-care preparations, e.g. pre-treatment preparations or leave-on products such as sprays, creams, gels, lotions, mousses and oils, or hair tonics, styling creams, styling gels, pomades, hair rinses, treatment packs, intensive hair treatments, hair-structuring preparations, e.g. hair-waving preparations for permanent waves (hot wave, mild,wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Of special importance as cosmetic preparations for the hair are the above-mentioned preparations for hair treatment, especially hair-washing preparations in the form of shampoos, hair conditioners, hair-care preparations, e.g. pre-treatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocoamidopropyl betaine, 3.0% by weight of sodium chloride, and water ad 100%.

A further embodiment of the present invention concerns micronised UV absorbers, for example:
- wet-grinding with a hard grinding medium, for example zirconium silicate and a protective surfactant or a protective polymer in water or in a suitable organic solvent;
- spray-drying from a suitable solvent, for example aqueous suspensions or suspensions containing organic solvents, or true solutions in water, ethanol, dichloroethane, toluene or N-methylpyrrolidone etc.;
- by the expansion according to the RESS process (Rapid Expansion of Supercritical Solutions) of supercritical fluids (e.g. $CO_2$) in which the UV filter or filters is/are dissolved, or the expansion of fluid carbon dioxide together with a solution of one or more UV filters in a suitable organic solvent;
- by reprecipitation from suitable solvents, including supercritical fluids (GASR process=Gas Anti-Solvent Recrystallisation/PCA process=Precipitation with Compressed Anti-solvents).

As grinding apparatus for the preparation of the micronised organic UV absorbers there may be used, for example, a jet mill, ball mill, vibratory mill or hammer mill, preferably a high-speed mixing mill. The grinding is preferably carried out with a grinding aid, for example an alkylated vinylpyrrolidone polymer, a vinylpyrrolidone/vinyl acetate copolymer, an acyl glutamate, an alkyl polyglucoside, ceteareth-25 or a phospholipid.

The micronised UV absorbers so obtained usually have an average particle size that is from 0.02 to 2 μm, preferably from 0.05 to 1.5 μm, and more especially from 0.1 to 1.0 μm.

The UV absorbers can also be used dry in powder form. For that purpose the UV absorbers are subjected to known grinding methods, such as vacuum atomization, countercurrent spray-drying etc. Such powders have a particle size of from 0.1 μm to 2 μm. To avoid the occurrence of agglomeration, the UV absorbers can be coated with a surface-active compound prior to the pulverisation process, for example with an anionic, non-ionic or amphoteric surfactant, e.g. a phospholipid or a known polymer, such as PVP, or an acrylate. The colouring compositions according to the invention may further comprise antimicrobial agents.

Preferred antimicrobial preservatives and antimicrobial actives used in formulations (in most cases the INCI name of the antimicrobial substances is mentioned):
formaldehyde and paraformaldehyde, hydroxy biphenyls and its salts such as ortho-phenylphenol, zinc pyrithion, chlorobutanol, hydroxy benzoic acids and their salts and esters such as methyl paraben, ethyl paraben, propyl paraben, butyl paraben, dibromo hexamidine and its salts including isothionate (4,4'-hexamethylenedioxy-bis(3-bromo-benzamidine) and 4,4'-hexamethylenedioxy-bis(3-bromo-benzamidinium 2-hydroxyethanesulfonate), mercury, (aceto-O)phenyl (especially phenyl mercuric acetate) and Mercurate(2-), (orthoborate(3-)-O)phenyl, dihydrogene (especially phenyl mercuric borate), 1,3-bis (2-ethylhexyl)-hexahydro-5-methyl-5-pyrimidine (Hexetidin), 5-bromo-5-nitro-1,3-dioxan, 2-bromo-2-nitro-1, 3-propandiol, 2,4-dichlorobenzyl alcohol, 3,4, 4'trichlorocarbanilide (Trichlorcarban), p-chloro-m-cresol, 2,4,4'-trichloro 2-hydroxy diphenylether (triclosan), 4,4'-dichloro 2-hydroxy diphenylether, 4-chloro-3,5-dimethylphenol (Chloroxylenol), imidazolidinyl urea, poly-(hexamethylene biguanide) hydrochloride, 2-phenoxy ethanol (phenoxyethanol), hexamethylene tetramine (Methenamine), 1-(3-chloroallyl)-3,5,7-triaza-1-azonia-adamantanchloride (Quaternium 15), 1-(4-chlorophenyoxy)-1-(1-imidazolyl)3,3-dimethyl-2-butanone (Climbazole), 1,3-bis(hydroxymethyl)-5,5-dimethyl-2,4-imidazolidinedione (DMDM hydantoin), benzyl alcohol, 1,2-dibromo-2,4-dicyano butane, 2,2' methylene-bis(6-bromo-4-chloro phenol) (bromochlorophene), methylchloroisothiazolone, methylisothiazolone, octylisothiazolone, benzylisothiazolone, 2-benzyl-4-chlorophenol (Chlorophenone), chloracetamide, chlorhexidine, chlorhexidine acetate, chlorhexidine gluconate, chlorhexidine hydrochloride, 1-phenoxy-propane-2-ol (phenoxyisopropanol), 4,4-dimethyl-1,3-oxazolidine (dimethyl oxazolidine), diazolidinyl urea, 4,4'-hexamethylenedioxybisbenzamidine and 4,4'-hexamethylenedioxy-bis(benzamidinium-2-hydroxyethanesulfonate), glutaraldehyde (1,5-pentanedial), 7-ethylbicyclooxazolidine, 3-(4-chlorophenoxy)-1,2-propandiol (chlorphenesin), phenylmethoxymethanol and ((phenylmethoxy)methoxy)-methanol (benzylhemiformal), N-alkyl(C12–C22) trimethyl ammoniumbromide and -chloride (cetrimonium bromide, cetrimonium chloride), benzyl-dimethyl-(4-(2-(4-(1,1,3,3-tetramethylbutyl)-phenoxy)-ethoxy)-ethyl)-ammoniumchloride (benzethonium chloride), Alkyl-(C8–C18)-dimethyl-benzylammonium chloride, -bromide and saccharinate (benzalkonium chloride, benzalkonium bromide, benzalkonium saccharinate), benzoic acid and its salts and esters, propionic acid and its salts, salicylic acid and its salt, sorbic acid and its salts, sodium iodiate, inorganic sulfites and bisulfites such as sodium sulfite, dehydroacetic acid, formic acid, mercurate(1-ethyl)2-mercaptobenzoate(2-)-O,S—, hydrogene (Thiomersal or Thiomerosal), 10-undecylenic acid and its salts, octopirox (piroctone olamine), sodium hydroxy methyl-aminoacetate (sodium hydroxymethylglycinate), 3-iodo-2-propynyl butylcarbamate, 10-undecylenic acid, sulfur.

Combinations with natural antimicrobials or chemically modified natural substances with antimicrobial activities such as chitosans and chitosan derivatives, famesol, plant extracts such as clove oil, blue cypres oil etc. can be also used.

For use on human hair, the dyeing compositions can usually be incorporated into an aqueous cosmetic carrier. Suitable aqueous cosmetic carriers include, for example, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially column 1, line 70 to column 3, line 55. The dyeing compositions according to the invention are also excellently suitable for the colouring method described in DE-A-3 829 870 using a colouring comb or a colouring brush.

Further carriers for dying compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, pages 248–250, especially on page 243, line 1 to page 244, line 12.

Suitable formulations of cationic dyes, which can be used in the colouring compositions according to the invention, are described for example in in WO 95/01772, especially on page 11, line 29 to page 12, line 7, or in WO 01/66646, especially on page 7, line 1 to page 22, and preferred from page 16, line 20 to page 22, or direct dyes as described in DE-A-19 713 698, especially page 3, line 51 to page 4, line 29 and page 4, line 65 to page 5, line 60, or direct dyes and oxidizing agent as described in WO 97/20545, especially on page 9, line 1 to page 11, line 4, in particular on page 11, line 6 to page 13, line 19.

Preferred formulations of cationic dyes with other dyes, which can be used in the colouring compositions according to the invention, are:

combinations of Pyrazolo-[1,5-a]-pyrimidines with at least one cationic dye as described in EP 998,908, especially on page 47, line 3 to page 49, line 26, and preferred on page 51, line 4 to page 52, line 5, or combinations of cationic dyes as described in FR-2788432, especially on page 53, line 1 to page 63, line 23, especially a combination of cationic dyes with Arianors in FR-2788432, especially on pages 51 to 52, or especially a combination with at least one Basic Brown 17, Basic brown 16, Basic Red 76 and Basic Red 118, and/or at least one Basic Yellow 57, and/or at least one Basic Blue 99, or combinations of direct dyes and/or an oxidation dye and oxidizing agents in the form of permanent-wave fixing solution, especially with direct dyes as described in DE-A-19 713 698, especially page 4, line 65 to page 35, line 59, or combinations of cationic dyes and an oxidation dye of the developer compound type and oxidizing agents as described in EP 850 638, especially on page 2, lines 3 to 12 and line 30 to page 14, and page 28, line 35 to page 30, line 20, preferred on page 30, line 25 to page 32, line 30, or ready-to-use dyeing compositions and multicompartment device for dyeing keratin fibers comprising combinations of an extemporaneous mixture of a composition (A) containing one or more oxidation dye precursors and optionally one or more couplers, and of a composition (B), in powder form, containing one or more direct dye, preferably cationic, optionally dispersed in an organic pulverulent excipient and/or a mineral pulverulent excipient, and a composition (C) containing one or more oxidizing agent as described in U.S. Pat. No. 6,190,421, especially in column 2, line 20 to line 31 in column 7, line 15 to column 8, line 43, and preferably in column 8, line 55 to column 9, line 56, and preferably with direct dyes as described in column 5, line 30 to column 7, line 14, or a ready-to-use composition comprising, at least one oxidation base, at least one cationic direct dye and at least one enzyme of 2-electron oxidoreductase type in the presence of at least one donor for the said enzyme as described in U.S. Pat. No. 6,228,129, especially in column 2, line 16 to column 25, line 55, and a multi-compartment dyeing device as described in column 26, lines 13 to 24, especially in column 26, line 26 to column 27, line 9, or a ready-to-use composition comprising compositions of at least one direct cationic dye and at least one nitrated benzene dye as described in WO 99/20235 especially on page 1, line 25 to page 8, line 5, and on page 30, line 17 to page 34 line 25, with cationic direct dyes as described on page 8, line 12 to page 25 line 6, and a multi-compartment dyeing device as described on page 35, lines 21 to 27, especially on page 36, line 1 to page 37, or a ready-to-use composition or a multi-compartment dyeing device comprising compositions of at least one direct cationic dye and at least one autooxidisable oxidation dye, especially benzene, indol and indoline derivatives as described in WO 99/20234, especially on page 26, line 5 to page 32, line 18, or oxidation dyeing compositions of at least one direct dye and at least one meta-Aminophenol derivative and at least one developer compound and an oxidizing agent as described in EP 850 636, especially on page 18, line 1 to page 22, line 11, or oxidation dyeing compositions of at least one direct dye and at least one developer compound selected from the group of para-Phenylenediamine derivatives and Bis-Phenylalkylenediamine and, and at least one coupler compound selected from the group of meta-Diphenols and an oxidizing agent, as described in EP-A-850 637, especially on page 19, line 24 to page 22, line 57, cationic dye and e.g. a pyrazolo-(1,5-a)-pyrimidine derivatives, as described in EP 998 908, especially on page 47, line 25 to page 50, line 29, or oxidative dye precursors (unsaturated aldehyde and coupler compounds), as described in German Patent Application 197 172 24, especially on page 3, line 36 to page 9 line 64.

Cationic dyes, especially compound of formula (1), (2) or (3) may be present in the colouring compositions according to the invention preferably in an amount of from 0.001% to 5%, especially from 0.01% to 1%, based on the total dyeing composition.

The pH value of the ready-to-use dyeing preparations is usually from 2 to 11, preferably from 5 to 10.

The constituents of the aqueous carrier are used in the colouring compositions to the invention in the amounts customary for that purpose; for example emulsifiers may be used in concentrations of from 0.5 to 30% by weight and thickeners in concentrations of from 0.1 to 25% by weight of the total dyeing composition.

If direct dyes, especially of compound of formula (1), (2) or (3) are used together with oxidation dyes and/or the addition salts thereof with an acid, they may be stored separately or together.

It is preferred to store the oxidation dyes and direct dyes, which are not stable to reduction, separately.

They may be stored in a liquid to paste-like preparation (aqueous or non-aqueous) or in the form of a dry powder.

When the dyes and adjuvants are stored together in a liquid preparation, the preparation should be substantially anhydrous in order to reduce reaction of the compounds.

When they are stored separately, the reactive components are intimately mixed with one another only immediately before use. In the case of dry storage, before use a defined amount of hot (from 50 to 80° C.) water is usually added and a homogeneous mixture prepared.

One preferred method of applying direct dyes containing formulations on hair is by using a multi-compartment dyeing device or "kit" or any other multi-compartment packaging system, as described for example in WO 97/20545 on page 4, line 19 to line 27.

The colouring compositions according to the invention may combined with a suitable ready-to-use composition for the oxidation dyeing of keratin fibers, in particular human keratin, comprising an oxidizing agent, at least one direct dye, especially compound of formula (1), (2) or (3) and at least one oxidation dye precursor, as described in U.S. Pat. No. 6,190,421, in column 1, line 65 to column 3, line 65, especially in column 10, line 62 to column 12, line 65. Preferably, such a ready-to-use composition is prepared according to a first preferred embodiment by a process which comprises a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler, especially selected from meta-phenylenediamines and the acid-addition salts thereof, and at least one cationic direct dye, especially compound of formula (I), on the other hand, a composition (B) containing, in a medium which is suitable for dyeing, at least one oxidizing agent and mixing them together at the time of use before applying this mixture to the keratin fibers.

According to a second preferred embodiment for the preparation of the ready-to-use dye composition, the process includes a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler compound, especially selected from meta-phenylenediamines and the acid-addition salts thereof; on the other hand, a composition (A') comprising, in a medium which is suitable for dyeing, at least one cationic direct dye, especially compound of formula (I), and, lastly, a composition (B) containing, in a medium which is suitable for dyeing, at least one oxidizing agent as defined above, and mixing them together at the time of use before applying this mixture to the keratin fibers.

The composition (A') used according to this second variant of the process in accordance with the invention can optionally be in powder form, the cationic direct dye(s) in accordance with the invention itself (themselves) constituting, in this case, all of the said composition (A') or optionally being dispersed in an organic and/or inorganic pulverulent excipient.

When it is present in the composition A', the organic excipient can be of synthetic or plant origin and is selected in particular from crosslinked and non-crosslinked synthetic polymers, polysaccharides such as celluloses and modified or unmodified starches, as well as natural products containing them such as sawdust and plant gums (guar gum, carob gum, xanthan gum, etc.).

When it is present in the composition (A'), the inorganic excipient can contain metal oxides such as titanium oxides, aluminium oxides, kaolin, talc, silicates, mica and silicas.

An very suitable excipient in the colouring compositions according to the invention is sawdust.

The powdered composition (A') can also contain binders or coating products in an amount, which preferably does not exceed approximately 3% by weight relative to the total weight of the said composition (A').

These binders are preferably selected from oils and liquid fatty substances of inorganic, synthetic, animal or plant origin.

The composition (A') may optionally also contain other adjuvants, in powdered form, in particular surfactants of any kind, hair conditioners such as, for example, cationic polymers, etc.

Another subject of the invention is a multi-compartment dyeing device or "kit" or any other multi-compartment packaging system, as described for example in U.S. Pat. No. 6,228,129, especially in column 26, lines 13 to 24, especially in column 26, line 26 to column 27, line 9, or. A first compartment which contains the composition (A) as defined above, an optional second compartment contains the composition (A') as defined above, when it is present, and a third compartment contains the oxidizing composition (B) as defined above. These devices can be equipped with means which allow the desired mixture to be applied to the hair, such as the devices described in French patent FR-2,586,913, the disclosure of which is specifically incorporated by reference herein.

An oxidizing agent, which may be added to the colouring compositions according to the invention containing composition, comprises an oxidizing agent and a base.

Further, this composition comprises for this oxidizing agent containing composition customary adjuvant and additives.

The formulations are for example a solution, especially a thickened watery or watery alcoholic solution, a cream, foam, a gel, a powder or an emulsion.

In general, preference is given to a cream formulation, a gel formulation or a foam formulation, and especially a foam formulation.

But, if stability- or solubility-problems arise it may of advantage to use powder formulation as for example described in DE 197 13 698, page 2, line 26 to 54 and page 3, line 51 to page 4, line 25, and page 4, line 41 to page 5 line 59.

The oxidizing agent (calculated as hydrogen peroxide) is present in this composition in 0.5 to 12% by weight, in particular from 1 to 6% by weight based on the totals weight of the oxidizing agent containing composition.

The pH-value of the oxidizing agent containing composition is usually about 2 to 7, and in particular about 3 to 6.

An oxidizing agent free composition, which may be added to the colouring compositions according to the invention, comprises a developer compound and a coupler compound and a reduction agent, or a developer compound or/and optionally a reduction agent, or a coupler compound and a reduction agent.

Further, an oxidizing agent free composition may additionally comprise a direct dye as for example described in German Patent Application 199 59 479, column 3, line 12 to line 16.

Additionally, the oxidizing agent free composition usually comprises customary adjuvant and additives. Preferred are those, which are described in German Patent Application, in column 3, line 17 to line 41.

The pH-value of the oxidizing agent free composition is usually about 3 to 11, and in particular about 5 to 10, and most particular about 9 to 10.

For adjusting the pH-value organic or inorganic acids, as for example described in German Patent Application 199 59 479, column 3, line 46 to line 53 are suitable.

The colouring compositions according to the invention may also be combined with hair dye compositions comprising an acid dye. Hair dye compositions comprising an acid dye are known. For example, they are described in "Dermatology", edited by Ch. Culnan, H. Maibach, Verlag Marcel Dekker Inc., New York, Basle, 1986, Vol. 7, Ch. Zviak, The Science of Hair Care, chapter 7, pages 248–250, especially on page 253 and 254. The hair dye compositions comprising an acid dye have a pH of 2–6, preferably 2–5, more preferably 2.5–4.0. If the pH is too low, the resulting composition may roughen the hair, scalp and hand skin due to an acid component in some cases. If the pH is too high, the penetration accelerating effect on the acid dye is lowered.

A compound of formula (1), (2) or (3) according to the present invention may also readily be used in combination with other dyes and/or adjuvants used in the colouring of hair, for example acid dye and an alkylene carbonate, as described in U.S. Pat. No. 6,248,314, especially in examples 1 and 2, or acid hair dye compositions comprise various kinds of organic solvents represented by benzyl alcohol as a penetrant solvent have good penetrability into hair, as described in Japanese Patent Application Laid-Open Nos. 210023/1986 and 101841/1995, or acid hair dye compositions with a water-soluble polymer or the like to prevent the drooping of the hair dye composition, as described for example in Japanese Patent Application Laid-Open Nos. 87450/1998, 255540/1997 and 245348/1996, or acid hair dye compositions with a water-soluble polymer of aromatic alcohols, lower alkylene carbonates, or the like as described in Japanese Patent Application Laid-Open No. 53970/1998 and Japanese Patent Invention No. 23911/1973.

Preferred keratin fibers are human hair.

The dyes or dye precursors are suitable for all-over colouring of the hair, that is to say when colouring the hair on a first occasion, and also for re-colouring subsequently, or colouration of locks or parts of the hair.

The dyes or dye precursors are applied to hair for example through massage in by hand, a comb, a brush, or a bottle, or a bottle, which is combined with a comb or a nozzle.

In general, the dyes or dye precursors are applied to the hair in a formulation with further components, like adjuvants or additional dyes or dye precursors.

After the application of the dyeing composition the dyed hair is customary rinsed. Customary, the rinsing is conducted with water.

In a suitable embodiment of the processes of the present invention for dyeing human hair, the dyeing composition is not rinsed off, but washed off with a commercially available hair shampoo.

In general, the dyed hair is dried after rinsing and/or washing.

Customary, drying is conducted with hot air by means of a drier or the like, since color migration to clothes and the like becomes scarcely caused.

A very suitable process for dyeing keratin fibers comprises contacting the keratin fibers under alkaline conditions with at least one capped diazotized compound and a coupler compound, with the proviso that the pH is adjusted in the range from 2 to 6 in the last process step. Adjusting the pH is achieved in conventional manner by adding an acid as described for example in EP 962218, especially on page 3, lines 12 to 16.

Acids are for example tartaric acid or citric acid, a citric acid gel, a suitable buffer solution with optionally an acid dye.

Preferred technical forms of acids are a solution, a gel, a cream, foam, a conditioner, a emulsion, a shampoo and more preferred a shampoo or a conditioner.

In the context of the present invention, the expression "alkaline condition", denotes to all process steps without those wherein acid conditions are explicitly described.

In the processes for colouring according to the invention, whether or not colouring is to be carried out in the presence of a further dye will depend upon the colour shade to be obtained.

In the context of the present invention, the expression "a further dye", denotes preferably an oxidation dye, a diazotised compound, a capped diazotised compound and/or coupler compound, or acid dye, especially selected a cationic, anionic or uncharged direct dye, especially a cationic dye selected from the group of the cationic dyes as described in WO 95/01772, especially on page 2, line 7 to page 4, line 1, and preferred on page 4, line 35 to page 8, line 21 with the given preferences, and as described in WO 01/66646, especially on page 1, line 18 to page 3, line 16, or a mixture of at least two cationic dyes as described in WO 95/01772, especially on page 8, line 34 to page 10, line 22.

The processes of the present invention for dyeing keratin fibers, in particular human hair, comprise after contacting the keratin fiber with at least a compound of formula (1), (2) or (3), and then leaving the fibers to stand, and then rinsing the fibers.

The process for dyeing is for example described in WO 01/66646 on page 15, line 32 to page 16, line 2.

Usually, the dyeing compositions are usually applied to the hair in an amount of from 50 to 100 g.

This composition is left on the fiber at 15 to 45° C. for 5 to 30 minutes, and in particular for 10 to 20 minutes at 20 to 30° C.

Further preferred does a process for dyeing keratin fibres comprise contacting the keratin fibers with at least one direct dye, a base and an oxidizing agent.

Compositions comprising at least one direct dye, especially compound of formula (1), (2) or (3) and an oxidizing agent, are for example described in WO 97/20545, on page 3, line 24 to page 11, line 4, and especially on page 4, line 9 to 17.

The composition comprising at least one direct dye, especially at least a compound of formula (1), (2) or (3), a base and an oxidizing agent is prepared by mixing at least one direct dye and a base, and then just before the dyeing of the hair, adding an oxidizing agent.

Alternatively, the oxidizing agent can be applied simultaneously with a composition comprising at least one dye, such as a compound of formula (1), (2) or (3) and a base.

Preferably, the process for dyeing keratin fibres with at least on direct dye comprises using a multi-compartment dyeing device or 'kits' as described for example in WO 97/20545, especially on page 4, line 19 to line 27.

Suitable processes for enlightening dyeing, wherein a compound of formula (1), (2) or (3) according to the invention can be used in combination with an oxidative agent are described in WO 97/20545, on page 11 to page 13.

Further preferred are processes for dyeing keratine fibers, especially compound of formula (1), (2) or (3) with further cationic dyes, according to processes as described in WO 95/01772, especially on page 10, line 24 to page 11, line 16, and especially on page 11, line 29 to page 28, or in WO 01/66646, especially on page 1, line 18 to page 3, line 16, and preferred from page 16, line 20 to page 22, or in EP 970 685, especially on page 50, lines 15 to 43, and preferred from page 50, line 46 to page 51, line 40, or in DE-A-19 713 698, especially page 5, lines 26 to 60, or a process of dyeing with direct dyes and oxidizing agent is described in WO 97/20545, especially on page 10, line 10 to page 11, line 55 and preferably on page 11, line 6 to page 13, line 19.

Further preferred are processes for dyeing keratine fibers, especially compound of formula (1), (2) or (3) with other dyes, which can be combined with a compound of formula (1), (2) or (3) according to the present invention, are:

mixtures of at least two cationic dyes as described in WO 95/01772, especially on page 11, lines 1 to 15, or combinations of Pyrazolo-[1,5-a]-pyrimidines with at least one cationic dye as described in EP 998,908, especially on page 50, lines 15 to 28, or combinations of cationic dyes as described in FR-2788432, especially on page 49, line 28 to page 52, and preferred on page 50, lines 16 to 28, or combinations of direct dyes and/or an oxidation dye and oxidizing agents in the form of permanent-wave fixing solution, especially with direct dyes as described in DE-A-19 713 698, especially on page 2, lines 12 to 23, especially on page 4, line 65 to page 5, line 59, or combinations of cationic dyes and an oxidation dye of the developer compound type and oxidizing agents as described in EP 850 638, especially on page 29, line 42 to page 30, line 20 and preferred on page 30, line 25 to page 32, line 30, or combinations of an extemporaneous mixture of a composition (A) containing one or more oxidation dye precursors and optionally one or more couplers, and of a composition (B), in powder form, containing one or more direct dye, preferably cationic, optionally dispersed in an organic pulverulent excipient and/or a mineral pulverulent excipient, and a composition (C) containing one or more oxidizing agent as described in U.S. Pat. No. 6,190,421, especially in column 8, lines 43 to 52, and preferably in column 8, line 55 to column 9, line 55, or a ready-to-use composition comprising, at least one oxidation base, at least one cationic direct dye and at least one enzyme of 2-electron oxidoreductase type in the presence of at least one donor for the said enzyme as described in U.S. Pat. No. 6,228,129, especially in column 25, line 56 to column 27, line 9, or a ready-to-use composition or multi-compartment dyeing device comprising compositions of at least one direct cationic dye and at least one nitrated benzene dye as described in WO 99/20235 on page 34, line 27 to page 37, or a ready-to-use composition or multi-compartment dyeing device comprising compositions of at least one direct cationic dye and at least one autooxidisable oxidation dye, especially benzene, indol and indoline derivatives as described in WO 99/20234, especially on page 32, line 20 to page 35, oxidation dyeing compositions of at least one direct dye and at least one meta-Aminophenol derivative and at least one developer compound and an oxidizing agent as described in EP 850 636, especially on page 18, line 1 to page 22, line 11, or oxidation dyeing compositions of at least one direct dye and at least one developer compound selected from the group of para-Phenylenediamine derivatives and Bis-Phenylalkylenediamine and, and at least one coupler compound selected from the group of meta-Diphenols and an oxidizing agent, as described in EP-A-850 637, especially on page 19, line 24 to page 22, line 57, cationic dye and e.g. a pyrazolo-(1,5-a)-pyrimidine derivatives, as described in EP 998 908, especially on page 47, line 25 to page 50, line 29, or arianors and/or oxidative dyes, as described in FR-2 788 432, especially on page 2, line 16 to page 3, line 16, and page 5, line 19 to page 14, line 8, and combinations with cationic dyes as described on page 14, line 23 and following, or oxidative dye precursors (unsaturated aldehyde and coupler compounds), as described in German Patent Application 197 172 24, especially on page 3, line 36 to page 9 line 64.

The processes of colouring of keratin fibers, especially human hair, with a compound of formula (1), (2) or (3) according to the present invention may be combined with other direct dyes and oxidative dyes.

In a preferred embodiment of the present invention the process for dyeing keratin fibers with direct dyes and oxidative dyes, in particular human hair, comprises
a) contacting the keratin fibers with an oxidizing agent, optionally containing at least a compound of formula (1), (2) or (3),
b) then contacting the keratin fibers with an oxidizing agent free composition, optionally containing at least a compound of formula (1), (2) or (3), or
a) contacting the keratin fibers with an oxidizing agent free composition, optionally containing at least a compound of formula (1), (2) or (3),
b) then contacting the keratin fibers with an-oxidizing agent, optionally containing least a compound of formula (1), (2) or (3), with the proviso that at least in one of the process steps a) or b) a compound of formula (1), (2) or (3) is present.

The process of colouring with a compound of formula (1), (2) or (3) according to the present invention may combined with a process for dyeing keratin fibers with direct dyes and oxidative dyes, which comprises contacting the keratin fibers with least a compound of formula (1), (2) or (3), then contacting the keratin fibers with an oxidizing agent free composition.

Such process is for example described in DE 199 41 450, especially on page 5, lines 50 to 58, and on page 8, line 31 to 46.

Oxidizing agent is usually applied in form of an oxidizing agent containing composition. Oxidizing agent free composition containing at least one coupler compound, at least one developer compound, a base and a reduction agent.

Customary, the oxidizing agent containing composition is evenly applied in a sufficient amount related to the amount of hair, usually with 30 to 200 g.

In general, the oxidizing agent containing composition is left on the fiber at 15 to 45° C. for 0 to 15 minutes, and in particular for 0 to 5 minutes.

Then the oxidizing agent free composition is applied to the hair.

In general, the direct dye and oxidizing agent free composition is left on the fiber at 15 to 50° C. for 5 to 45 minutes, and in particular for 10 to 25 minutes.

The coupler and developer compounds of the oxidizing agent free composition can be applied simultaneously or in succession. Preferred is a simultaneous application.

One preferred embodiment of the process is to wash the hair with shampoo and or a weak acid, such as citric acid or tartrate acid.

The direct dyes, which are stable to reduction can stored together with the oxidizing agent free compositions and are applicable as composition.

It is of advantage to prepare compositions of direct dyes, which are not stable to reduction, with oxidizing agent free compositions just before the dyeing process.

Further, a direct dye and an oxidizing agent free composition can be applied simultaneously or in succession.

A further process for the coloration of keratin fiber with direct dyes and oxidation dyes, which can be used in combination with a compound of formula (1), (2) or (3) according to the invention, comprises mixing at least a compound of formula (1), (2) or (3) and optionally at least one coupler compound and at least one developer compound, and an oxidizing agent, which optionally contains at least one further direct dye, and then contacting the keratin fibers with the mixture as prepared in step a).

A further suitable process for the coloration of keratin fiber with direct dyes and oxidation dyes, which can be used in combination with a compound of formula (i), (2) or (3) according to the invention, comprises mixing at least one autooxidable compound and at least one developer compound and at least one compound of formula (1), (2) or (3), and then contacting the keratin fibers with the mixture prepared in step a).

The present invention relates also to a process, in which a dye of formula (1), (2) or (3), or cationic dye of formula (1), (2) or (3) prepared according to a process according to the invention, or a composition according to the invention, and, in succession in any desired order, or simultaneously, a capped diazonium compound and a water-soluble coupling component, are applied to the material to be dyed under conditions in which coupling does not take place initially, and then the capped diazonium compound disposed on the material is caused to react with the coupling component.

The first step of the dyeing method according to the invention comprises applying to the material to be dyed, in succession in any order or simultaneously, a capped diazonium compound and a water-soluble coupling component and, optionally, a cationic direct dye, the application being carried out under such conditions that coupling does not take place initially.

This is effected, for example, by immersing the material in a solution comprising the capped diazonium compound or the coupling component and, optionally, a cationic direct dye, and then, if desired after rinsing and intermediate drying, immersing the material in a solution of the second component. Preferably, however, the capped diazonium compound and the coupling component and, optionally, a cationic direct dye, are present together in one solution. Such solutions can also be applied to the material by spraying or by similar measures, care having to be taken that penetration is adequate unless it is desired to dye only the upper layers. In that first step, the diazonium compound and the coupling component should not yet react with each other, and that is preferably achieved by maintaining a pH value of from 8 to 12, preferably from 9 to 11.

In the second step, the diazonium compound and the coupling component are then caused to react, preferably by lowering the pH to a value of from 5 to 2, especially from 3 to 4. The pH value is lowered in customary manner by addition of an acid or a suitable buffer solution, especially citric acid or citric acid gel. If desired, a cationic direct dye may be used in the second step. In any event, it is necessary for a cationic direct dye to be used in one of steps 1 and 2 of the process according to the invention.

The dyed material is then finished in conventional manner, for example by rinsing with water and subsequently drying.

Further, in the present invention especially preferred is a process for dyeing keratin fibers, in particular human hair, with capped diazotised compounds, which comprises, contacting the keratin fibers, under alkaline conditions, with at least one capped diazotised compound and a coupler compound, and optionally an oxidising agent, and optionally in the presence of a further dye, and optionally with at least a compound of formula (1), (2) or (3), then adjusting the pH in the range of 6 to 2 by treatment with acid, optionally in the presence of a further dye, especially with, and optionally at least a compound of formula (1), (2) or (3), with the proviso that at least in one step d) or e) at least a compound of formula (1), (2) or (3) is present.

The capped diazotised compound and coupler compound and optionally the oxidizing agent, can be applied in any desired order successively, or simultaneously.

Preferably, however, the capped diazotised compound and the coupler compound are applied simultaneously, in a single composition.

Customary the dyeing composition is applied to the hair in an amount of from 50 to 100 g.

In the context of the present invention, the expression "alkaline conditions" denotes a pH in the range from 8 to 10, preferably 9–10, especially 9.5–10.

Adding bases, for example sodium carbonate, ammonia or sodium hydroxide, to the hair or to the dye precursors, the capped diazotised compound and/or the water-soluble coupling component, or to colouring compositions comprising the dye precursors, customarily achieve the alkaline conditions.

In the second stage, the diazotised compound and the coupler compound are then caused to react, preferably by lowering the pH by adding an acid to a value of from 6 to 2, especially from 3 to 4.

Acids are for example tartaric acid or citric acid, a citric acid gel, a suitable buffer solution with optionally an acid dye.

Preferred technical forms of acids are a solution, a gel, a cream, foam, a conditioner, a emulsion, a shampoo and more preferred a shampoo or a conditioner.

The ratio of the amount of alkaline colouring composition applied in the first stage to that of acid colouring composition applied in the second stage is preferably about from 1:3 to 3:1, especially about 1:1.

This first alkaline and then acid dyeing compositions each are left on the fiber at 15 to 45° C. for 5 to 60 minutes, and in particular for 5 to 45 minutes at 20 to 30° C.

A preferred embodiment of the process for dyeing keratin fibres with capped diazotised compounds and a coupler compound, comprises contacting the keratin fibres with more than one capped diazotised compound and/or more than one coupler compound.

Preferred is a process of the present invention for the coloration of keratin fiber with capped diazotised compounds and at least a compound of formula (1), (2) or (3), comprises mixing, under alkaline conditions, at least one with capped diazotised compound and at least one coupler compound and, optionally with at least a compound of formula (I), and optionally at least one developer compound; and an oxidizing agent, and, optionally with at least a compound of formula (1), (2) or (3), and then contacting the keratin fibers with the mixture as prepared in step a), and then adjusting the pH in the range of 6 to 2 by treatment with acid, optionally in the presence of a further dye, with the proviso that at least in one of the process a compound of formula (1), (2) or (3) is present.

More preferred is a process for dyeing keratin fibres with at least one capped diazotized compound, which comprises mixing under alkaline conditions, at least one capped diazotized compound and at least a compound of formula (1), (2) or (3), a base and an oxidizing agent, and then contacting the keratin fibers with the mixture as prepared in step a), then adjusting the pH in the range of 6 to 2 by treatment with acid, optionally in the presence of a further dye.

Further, preferred is a process for the coloration of keratin fiber with capped diazotised compounds comprising mixing under alkaline conditions, at least one with capped diazotised compound and at least one coupler compound and optionally at least a compound of formula (1), (2) or (3), and optionally at least one developer compound, and optionally at least one autooxidable compound, and then contacting the keratin fibers with the mixture prepared in step a), then adjusting the pH in the range of 6 to 2 by treatment with acid, and and optionally at least a compound of formula (1), (2) or (3), and optionally in the presence of a further dye, with the proviso that at least in one of the process a compound of formula (1), (2) or (3) is present.

A further preferred process for the two-step direct dyeing of keratin fibres, which can be used in combination with a compound of formula (1), (2) or (3) according to the invention, is characterized in that, contacting the keratin fibers with an oxidizing agent or an oxidizing agent containing composition, then contacting the keratin fibers with at least one capped diazotised compound and at least a coupler compound and a compound of formula (1), (2) or (3), and optionally an oxidizing agent free composition, then adjusting the pH in the range of 6 to 2 by treatment with acid, optionally in the presence of a further dye or contacting the keratin fibers with at least one capped diazotised compound and a coupler compound and a compound of formula (1), (2) or (3), and optionally an oxidizing agent free composition, then contacting the keratin fibers with an oxidizing agent or an oxidizing agent containing composition, then adjusting the pH in the range of 5 to 2 by treatment with acid, optionally in the presence of a further dye.

The present invention also concerns a process for the colouration of keratin fibers, especially human hair, with acid dyes, which can be used in combination with a compound of formula (1), (2) or (3) according to the invention.

The process comprises contacting the keratin fiber with an acid dye and at least a compound of formula (1), (2) or (3).

Customary, the dyeing composition comprising an acid dye is applied to the hair in an amount of from 50 to 100 g.

This in a composition is left on the fiber at 15 to 45° C. for 1 to 30 minutes, and in particular for 0 to 15 minutes at 20 to 30° C.

Preferably the hair is rinsed and than washed with shampoo and more preferably not rinsed, but washed with shampoo.

The shampoo used herein includes a shampoo comprising 5–20% of a usual anionic surfactant such as an alkylsulfate or polyoxyethylene alkylsulfate.

Further, the present invention relates to a method of dyeing keratin-containing fibres with the cationic reactive dyes, which comprises treating the fibres with the cationic reactive dyes defined at the beginning or with the dye compositions according to the invention.

A preferred embodiment of the method according to the invention for dyeing keratin-containing fibres comprises treating the fibres with a dyeing solution, prepared according to the process of the invention, comprising a tinctorially effective amount of a cationic reactive dye of formula (1), (2) or (3).

The cationic reactive dyes defined at the beginning are present in the dye compositions according to the invention preferably in a tinctorially effective amount of from 0.001% to 5%, especially from 0.01% to 1%, based on the total dyestuff.

The keratin-containing fibres are usually treated with the dyeing solution for about 30 minutes at 20–25° C.

A further preferred embodiment of the present invention relates to a method of dyeing hair, which comprises treating the hair with a) an acidic or alkaline permanent-wave solution, and b) then with a dyeing solution, prepared according to the process of the invention, comprising a cationic reactive dye of formula (1), (2) or (3).

Usually the keratin-containing fibres are treated with the permanent-wave solution for about 3–10 minutes, preferably for 4–6 minutes, at 20–25° C.

It is generally advisable to rinse the hair after treatment with the dyeing solution and/or permanent-wave solution.

The present invention relates also to the use of the cationic reactive dyes defined at the beginning or of the dye compositions according to the invention for dyeing keratin fibers, wool, leather, silk, cellulose or polyamides, especially for dyeing hair.

A preferred embodiment of the process according to the invention for dyeing keratin-containing fibres comprises treating the fibres with a dyeing solution, prepared according to the process of the invention, comprising a tinctorially effective amount of a cationic reactive dye.

The cationic reactive dyes are present in the dye compositions according to the invention preferably in a tinctorially effective amount of from 0.001% to 5%, especially from 0.01% to 1%, based on the total dyestuff.

The keratin-containing fibres are usually treated with the dyeing solution for about 30 minutes at 20–25° C.

A further preferred embodiment of the present invention relates to a method of dyeing hair, which comprises treating the hair with a) an acidic or alkaline permanent-wave solution, and b) then with a dyeing solution, prepared according to the process of the invention, comprising a cationic reactive dye.

Usually the keratin-containing fibres are treated with the permanent-wave solution for about 3–10 minutes, preferably for 4–6 minutes, at 20–25° C.

A preferred embodiment of the present invention relates to a method of dyeing hair, which comprises treating the hair with a mixture of a) an acidic or alkaline permanent-wave solution comprising a thiol derivative, and b) a dyeing solution comprising a cationic dichlorotriazine reactive dye or a cationic monofluoromonochloropyrimidine reactive dye.

The dyes according to the invention are distinguished by brilliant shades. They are suitable for dyeing organic material, such as keratin, wool, leather, silk, cellulose or polyamides, especially keratin-containing fibres, cotton or nylon, and preferably human hair. The dyeings obtained are distinguished by their depth of shade and their good fastness to washing properties, such as, for example, fastness to light, shampooing and rubbing. The stability and storage stability of the dyes according to the invention are excellent. They are accordingly especially suitable for dyeing under oxidising and reducing conditions. The advantage of the new dyes according to the present invention is their stability against reduction agents e. g. sodium sulfite and ascorbic acid. Therefore you can combine them with oxidation dyes in one emulsion.

The following Examples serve to illustrate the processes for colouration without limiting the processes thereto. Unless specified otherwise, parts and percentages relate to weight. The amounts of dye specified are relative to the material being coloured.

EXAMPLES G (APPLICATION)

Compositions A, B, C, D, E, F and G for colouring human hair according to the following table below.

| Compositions | A | B | C | D1–D21** | E6–E21**** | F* | G4–G14*** |
|---|---|---|---|---|---|---|---|
| cetyl stearyl alcohol | 11.00 | 11.00 | 11.00 | 11.00 | 11.00 | | 11.00 |
| oleth-5 | 5.0 | 5.0 | 5.0 | 5.0 | 5.0 | | 5.0 |
| oleic acid | 2.5 | 2.5 | 2.5 | 2.5 | 2.5 | | 2.5 |
| stearic acid monoethanolamide | 2.5 | 2.5 | 2.5 | 2.5 | 2.5 | | 2.5 |
| coconut fatty acid monoethanolamide | 2.5 | 2.5 | 2.5 | 2.5 | 2.5 | | 2.5 |
| sodium lauryl sulfate | 1.7 | 1.7 | 1.7 | 1.7 | 1.7 | | 1.7 |
| 1,2-propanediol | 1.0 | 1.0 | 1.0 | 1.0 | 1.0 | | 1.0 |
| ammonium chloride | 0.5 | 0.5 | 0.5 | 0.5 | 0.5 | | 0.5 |
| EDTA, tetrasodium salt | 0.2 | 0.2 | 0.2 | 0.2 | 0.2 | | 0.2 |
| perfume | 0.4 | 0.4 | 0.4 | 0.4 | 0.4 | | 0.4 |
| wheat protein hydrolysate | 0.2 | 0.2 | 0.2 | 0.2 | 0.2 | | 0.2 |
| silica | 0.1 | 0.1 | 0.1 | 0.1 | 0.1 | | 0.1 |
| 2,5-diaminotoluene sulfate | | | 0.7 | | 0.7 | | |
| 4-amino-2-hydroxytoluene | | | 0.5 | | 0.5 | | |
| 2,5,6-triamino-4-hydroxypyrimidine sulfate | | | 0.2 | | 0.2 | | |
| sodium sulfite | | | 1.0 | | 1.0 | | |
| ascorbic acid | | | 0.5 | | 0.5 | | |
| triazene of Example 15a | 9.33 | | | | | | |
| coupler of Example 15 | | 12.03 | | | | | |
| Direct dye** | | | | 0.4 | | | |
| Direct dye*** | | | | | | | 0.4 |
| Direct dye**** | | | | | 0.4 | | |
| Black Color No. 401 | | | | | | 0.1 | |
| Purple Color 401 | | | | | | 0.05 | |
| Orange Color No. 205 | | | | | | 0.1 | |
| benzyl alcohol | | | | | | 2.0 | |
| ethylene carbonate | | | | | | 10 | |
| propylene carbonate | | | | | | 15 | |
| ethanol | | | | | | 10 | |
| lactic acid | | | | | | 3.5 | |
| sodium carbonate solution | | | | | | of pH 2.9 | |
| hydroxyethyl cellutose | | | | | | 1.5 | |
| ammonia (25%) | 9.2 | 9.2 | 9.2 | 9.2 | 9.2 | | 9.2 |
| composition: pH | 9.8 | 9.8 | 9.8 | 9.8 | 9.8 | | 9.8 |
| water | ad 100 | ad 100 | ad 100 | ad 100 | ad 100 | ad 100 | ad 100 |

*F: dye mixture known from U.S. Pat. No. 6,248,314
**D1–D10 comprise the following dyes:
in D1 the direct dye** is Basic Yellow 87;
in D2 the direct dye** is Basic Orange 31;
in D3 the direct dye** is or Basic Red 51;
in D4 the direct dye** is the cationic dye of example 4 as described in WO 01/66646;
in D5 the direct dye** is the cationic dye of example 6, compound of formula 106, as described WO 02/31056;
in D6 the direct dye** has the following formula (I)

-continued

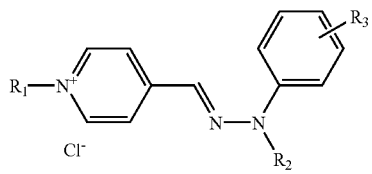

(I)

wherein
R₁ is methyl, R₂ is benzyl, R₃ is hydrogen;
in D7 the direct dye** is a compound of formula (I) wherein
R₁ is benzyl, R₂ is benzyl, R₃ is hydrogen;
in D8 the direct dye** is a compound of formula (I) wherein
R₁ is benzyl, R₂ is methyl, R₃ is hydrogen.
In D10 the direct dye** is a cationic dye of formula (3) as described in EP-A-714,954.
D11–D21 and *G4–G14 comprise the following direct dyes:
in D11 the direct dye and in G4 direct dye* is a compound of formula (4),
wherein X⁻ is chloride;
in D12 the direct dye and in G5 direct dye* is a compound of formula (5),
wherein X⁻ is chloride;
in D13 the direct dye and in G6 direct dye* is a compound of formula (6),
wherein X⁻ is chloride;
in D14 the direct dye and in G7 direct dye* is a compound of formula (7),
wherein X⁻ is chloride;
in D15 the direct dye and in G8 direct dye* is a compound of formula (8),
wherein X⁻ is chloride;
in D16 the direct dye and in G9 direct dye* is a compound of formula (9),
wherein X⁻ is iodide;
in D17 the direct dye and in G10 direct dye* is a compound of formula (10),
wherein X⁻ is chloride;
in D18 the direct dye and in G11 direct dye* is a compound of formula (11),
wherein X⁻ is chloride;
in D19 the direct dye and in G12 direct dye* is a compound of formula (12),
wherein X⁻ is chloride;
in D20 the direct dye and in G13 direct dye* is a compound of formula (13),
wherein X⁻ is chloride;
in D21 the direct dye and in G14 direct dye* is a compound of formula (14)
wherein X⁻ is chloride;.
**E6–E21: In E6 the direct dye is identical the direct dye of D6;
in E7 the direct dye** is identical the direct dye of D7;
in E8 the direct dye** is identical the direct dye of D8;
E9 comprises as direct dye Basic Yellow 87.
in E10 the direct dye** is identical the direct dye of D10;
in E11 the direct dye** is identical the direct dye of D11;
in E12 the direct dye** is identical the direct dye of D12;
in E13 the direct dye** is identical the direct dye of D13;
in E14 the direct dye** is identical the direct dye of D14;
in E15 the direct dye** is identical the direct dye of D15;
in E16 the direct dye** is identical the direct dye of D16;
in E17 the direct dye** is identical the direct dye of D17;
in E18 the direct dye** is identical the direct dye of D18;
in E19 the direct dye** is identical the direct dye of D19;
in E20 the direct dye** is identical the direct dye of D20;
in E21 the direct dye** is identical the direct dye of D21.

Example G/3

A strand of middle blond undamaged human hair is coloured
3a) with a mixture of 20 g of 6% hydrogen peroxide solution and a composition consisting of 5 g each of compositions A, B, C and G5, and alternatively
3b) first with 20 g of 6% hydrogen peroxide solution and then with 5 g of a composition A, 5 g of composition B, 5 g of composition C and 5 g of composition G6, or
3c) first with 5 g of a composition A, 5 g of composition B, 5 g of composition C and 5 g of composition G13, and then with 20 g of 6% hydrogen peroxide solution.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking red coloration having good fastness to washing and fastness to rubbing properties is obtained.

Example G/4

A strand of blond undamaged human hair is coloured
4a) with a composition consisting of 5 g each of compositions A, B and G10, and alternatively the colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking red coloration having good fastness to washing and fastness to rubbing properties is obtained.

Example (4a/G9) is identical to Example 4a with the proviso that G10 is replaced by G9.

Example (4a/G13) is identical to Example 4a with the proviso that G10 is replaced by G13.

Example G/5

A strand of middle blond undamaged human hair is coloured
5a) with a mixture of 15 g of 6% hydrogen peroxide solution and a composition consisting of 5 g each of compositions A, B and G6, and alternatively
5b) first with 15 g of 6% hydrogen peroxide solution, and then with 5 g of a composition A, 5 g of composition, and B and 5 g of composition G6.
5c) first with 5 g of a composition A, 5 g of composition, and B and 5 g of composition G6, and then with 15 g of 6% hydrogen peroxide solution.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking red coloration having good fastness to washing and fastness to rubbing properties is obtained.

Example (5a/G5) is identical to Example 5a with the proviso that G6 is replaced by G5.

Example (5a/G10) is identical to Example 5a with the proviso that G6 is replaced by G10.

Example (5b/G9) is identical to Example 5b with the proviso that G6 is replaced by G9.

Example (5b/G13) is identical to Example 5b with the proviso that G6 is replaced by G13.

Example (5c/G5) is identical to Example 5c with the proviso that G6 is replaced by G5.

Example (5c/G 13) is identical to Example 5c with the proviso that G6 is replaced by G13.

Example G/6

A strand of middle blond undamaged human hair is coloured
6a) with a mixture of 15 g of 6% hydrogen peroxide solution and a composition consisting of 5 g each of compositions A, B and G6, and alternatively
6b) first with 15 g of 6% hydrogen peroxide solution, and then with 5 g of a composition A, 5 g of composition B and 5 g of composition G6, or
6c) first with 5 g of a composition A, 5 g of composition B and 5 g of composition G6, and then with 15 g of 6% hydrogen peroxide solution.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking red coloration having good fastness to washing and fastness to rubbing properties is obtained.

Example (6a/G5) is identical to Example 6a with the proviso that G6 is replaced by G5.

Example (6a/G13) is identical to Example 6a with the proviso that G6 is replaced by G13.

Example (6b/G9) is identical to Example 6b with the proviso that G6 is replaced by G9.

Example (6b/G10) is identical to Example 6b with the proviso that G6 is replaced by G10.

Example (6c/G5) is identical to Example 6c with the proviso that G6 is replaced by G5.

Example (6c/G13) is identical to Example 6c with the proviso that G6 is replaced by G13.

Example G/9

A strand of blond undamaged human hair is coloured
9a) with a mixture of 10 g of 6% hydrogen peroxide solution and a composition consisting of 5 g each of compositions C and G6, and alternatively
9b) with 10 g of 6% hydrogen peroxide solution and 5 g of composition C and 5 g of composition G6.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking bluish red coloration having good fastness to washing and fastness to rubbing properties is obtained.

Example (9a/G5) is identical to Example 9a with the proviso that G6 is replaced by G5.

Example (9a/G13) is identical to Example 9a with the proviso that G6 is replaced by G3.

Example (9b/G9) is identical to Example 9b with the proviso that G6 is replaced by G9.

Example (9b/G10) is identical to Example 9b with the proviso that G6 is replaced by G10.

Example G/10

A strand of blond undamaged human hair is coloured
10a) with a mixture of 10 g of 6% hydrogen peroxide solution and a composition consisting of 5 g each of compositions D1 and E11, and alternatively
10b) first with 10 g of 6% hydrogen peroxide solution, and then with 5 g of composition D1 and 5 g of composition E11, or
10c) first with 5 g of composition D1 and 5 g of composition E11, and then with 10 g of 6% hydrogen peroxide solution.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking bluish red coloration having good fastness to washing and fastness to rubbing properties is obtained.

Example (10a/D2) is identical to Example 10a with the proviso that D1 is replaced by D2.

Example (10a/D3) is identical to Example 10a with the proviso that D1 is replaced by D3.

Example (10a/D4) is identical to Example 10a with the proviso that D1 is replaced by D4.

Example (10a/D5) is identical to Example 10a with the proviso that D1 is replaced by D5.

Example (10b/D2) is identical to Example 10b with the proviso that D1 is replaced by D2.

Example (10b/D3) is identical to Example 10b with the proviso that D1 is replaced by D3.

Example (10b/D4) is identical to Example 10b with the proviso that D1 is replaced by D4.

Example (10b/D5) is identical to Example 10b with the proviso that D1 is replaced by D5.

Example (10c/D2) is identical to Example 10c with the proviso that D1 is replaced by D2.

Example (10c/D3) is identical to Example 10c with the proviso that D1 is replaced by D3.

Example (10c/D4) is identical to Example 10c with the proviso that D1 is replaced by D4.

Example (10c/D5) is identical to Example 10c with the proviso that D1 is replaced by D5.

Example (10d/E12) is identical to Example 10a with the proviso that E11 is replaced by E12.

Example (10d/E19) is identical to Example 10a with the proviso that E11 is replaced by E19.

Example (10d/E16) is identical to Example 10a with the proviso that E11 is replaced by E16.

Example (10e/E15) is identical to Example 10b with the proviso that E11 is replaced by E15.

Example (10e/E12) is identical to Example 10b with the proviso that E11 is replaced by E12.

Example (10e/E16) is identical to Example 10b with the proviso that E11 is replaced by E16.

Example (10f/E12) is identical to Example 10c with the proviso that E11 is replaced by E12.

Example (10f/E19) is identical to Example 10c with the proviso that E11 is replaced by E19.

Example (10f/E16) is identical to Example 10c with the proviso that E11 is replaced by E16.

Example G/11

A strand of brown undamaged human hair is coloured 11a) with a mixture of 10 g of 6% hydrogen peroxide solution and a composition consisting of 5 g each of compositions C and E11, and alternatively 11b) first with 10 g of 6% hydrogen peroxide solution, and then with 5 g of composition C and 5 g of composition E11, or 11c) first with 5 g of composition C and 5 g of composition E11, and then with 10 g of 6% hydrogen peroxide solution.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking bluish red coloration having good fastness to washing and fastness to rubbing properties is obtained.

Example (11a/E12) is identical to Example 11a with the proviso that E11 is replaced by E12.

Example (11a/E19) is identical to Example 11a with the proviso that E11 is replaced by E19.

Example (11a/E16) is identical to Example 11a with the proviso that E11 is replaced by E16.

Example (11b/E15) is identical to Example 11b with the proviso that E11 is replaced by E15.

Example (11b/E19) is identical to Example 11b with the proviso that E11 is replaced by E19.

Example (11b/E12) is identical to Example 11b with the proviso that E11 is replaced by E12.

Example (11c/E12) is identical to Example 11c with the proviso that E11 is replaced by E12.

Example (11c/E19) is identical to Example 11c with the proviso that E11 is replaced by E19.

Example (11c/E15) is identical to Example 11c with the proviso that E11 is replaced by E15.

Example G/12

A strand of blond undamaged human hair is coloured 12a) with a mixture of 5 g of 6% hydrogen peroxide solution and 5 g of composition G6, and alternatively 12b) first with 5 g of 6% hydrogen peroxide solution, and then with 5 g of a composition G6, or 12c) first with 5 g of a composition G6, and then with 5 g of 6% hydrogen peroxide solution.

The colouring mixture is allowed to act on the hair for 30 minutes at about 22° C. After contact for 30 minutes, without being washed out, 10 g of a dye mixture F is applied to the hair. The hair is then combed through thoroughly, whereupon its pH becomes about 3. Then, after a contact period of 15 minutes, the hair is rinsed thoroughly with water and dried.

Example (12a/G5) is identical to Example 12a with the proviso that G6 is replaced by G5.

Example (12a/G13) is identical to Example 12a with the proviso that G6 is replaced by G13.

Example G/13

A strand of blond undamaged human hair is coloured with 10 g of composition G6, The colouring mixture is allowed to act on the hair for 30 minutes at about 22° C. After contact for 30 minutes, without being washed out, 10 g of a dye mixture F is applied to the hair. The hair is then combed through thoroughly, whereupon its pH becomes about 3. Then, after a contact period of 15 minutes, the hair is rinsed thoroughly with water and dried.

Example (13/G5) is identical to Example G/13 with the proviso that G6 is replaced by G5.

Example (13/G9) is identical to Example G/13 with the proviso that G6 is replaced by G9.

Example G/15

A strand of blond undamaged human hair is coloured with 10 g of a composition G6.

The colouring mixture is allowed to act on the hair for 30 minutes at about 22° C. After contact the strand is rinsed thoroughly, shampooed and then dried.

A strong, intense, striking red coloration having good fastness to washing and fastness to rubbing properties is obtained.

Example (15/G5) is identical to Example 15 with the proviso that G6 is replaced by G5.

Example (15/G9) is identical to Example 15 with the proviso that G6 is replaced by G9.

Example G/16

A strand of blond undamaged human hair is coloured 16a) with a mixture of 5 g of 6% hydrogen peroxide solution and 5 g of composition G6, and alternatively 16b) first with 5 g of 6% hydrogen peroxide solution, and then with 5 g of a composition G6, or 16c) first with 5 g of a composition G6, and then with 5 g of 6% hydrogen peroxide solution.

The colouring mixture is allowed to act on the hair for 30 minutes at about 22° C. 10 g of a 2% strength aqueous citric acid gel are then applied to the strand. After contact for 15 minutes, the strand is rinsed thoroughly, shampooed and then dried.

A strong, intense, striking red coloration having good fastness to washing and fastness to rubbing properties is obtained.

Example (16a/G5) is identical to Example 16a with the proviso that G6 is replaced by G5.

Example (16a/G9) is identical to Example 16a with the proviso that G6 is replaced by G9.

Example (16b/G10) is identical to Example 16b with the proviso that G6 is replaced by G10.

Example (16b/G13) is identical to Example 16b with the proviso that G6 is replaced by G13.

Example (16c/G13) is identical to Example 16c with the proviso that G6 is replaced by G13.

Example (16c/G5) is identical to Example 16c with the proviso that G6 is replaced by G5.

Example G/22

A strand of blond undamaged human hair is coloured with 10 g of a composition G6. Then the pH is adjusted in the range of pH 5 to 8 by adding citric acid.

The colouring mixture is allowed to act on the hair for 30 minutes at about 22° C. After contact the strand is rinsed thoroughly, shampooed and then dried.

A strong, intense, striking red coloration having good fastness to washing and fastness to rubbing properties is obtained.

Example (22/G5) is identical to Example G/22 with the proviso that G6 is replaced by G5.

Example (22/G13) is identical to Example G/22 with the proviso that G6 is replaced by G13.

Example G/23

A strand of brown undamaged human hair is coloured
11a) with a mixture of 15 g of 6% hydrogen peroxide solution and a composition consisting of 5 g each of compositions C, D1 and E11, and alternatively
11b) first with 10 g of 6% hydrogen peroxide solution, and then with 5 g each of compositions C, D1 and E11 or
11c) first with 5 g each of compositions C, D1 and E11, then with 10 g of 6% hydrogen peroxide solution.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking bluish red coloration having good fastness to washing and fastness to rubbing properties is obtained.

Example (23a/D2) is identical to Example 23a with the proviso that D1 is replaced by D2.

Example (23a/D3) is identical to Example 23a with the proviso that D1 is replaced by D3.

Example (23a/D4) is identical to Example 23a with the proviso that D1 is replaced by D4.

Example (23a/D5) is identical to Example 23a with the proviso that D1 is replaced by D5.

Example (23b/D2) is identical to Example 23b with the proviso that D1 is replaced by D2.

Example (23b/D3) is identical to Example 23b with the proviso that D1 is replaced by D3.

Example (23b/D4) is identical to Example 23b with the proviso that D1 is replaced by D4.

Example (23b/D5) is identical to Example 23b with the proviso that D1 is replaced by D5.

Example (23c/D2) is identical to Example 23c with the proviso that D1 is replaced by D2.

Example (23c/D3) is identical to Example 23c with the proviso that D1 is replaced by D3.

Example (23c/D4) is identical to Example 23c with the proviso that D1 is replaced by D4.

Example (23c/D5) is identical to Example 23c with the proviso that D1 is replaced by D5.

Example (23a/E12) is identical to Example 23a with the proviso that E11 is replaced by E12.

Example (23a/E16) is identical to Example 23a with the proviso that E11 is replaced by E16.

Example (23a/E15) is identical to Example 23a with the proviso that E11 is replaced by E15.

Example (23b/E12) is identical to Example 23b with the proviso that E11 is replaced by E12.

Example (23b/E19) is identical to Example 23b with the proviso that E11 is replaced by E19.

Example (23b/E15) is identical to Example 23b with the proviso that E11 is replaced by E15.

Example (23c/E16) is identical to Example 23c with the proviso that E11 is replaced by E16.

Example (23c/E12) is identical to Example 23c with the proviso that E11 is replaced by E12.

Example (23c/E19) is identical to Example 23c with the proviso that E11 is replaced by E19.

Example (23a/D2/E712) is identical to Example 23a/D2 with the proviso that that E11 is replaced by E12.

Example (23a/D3/E15) is identical to Example 23a/D3 with the proviso that that E11 is replaced by E15.

Example (23a/D4/E9) is identical to Example 23a/D4 with the proviso that E11 is replaced by E7.

Example (23b/D2/E19) is identical to Example 23b/D2 with the proviso that that E11 is replaced by E19.

Example (23b/D3/E12) is identical to Example 23b/D3 with the proviso that that E11 is replaced by E12.

Example (23b/D4/E16) is identical to Example 23b/D4 with the proviso that E11 is replaced by E16.

Example (23c/D2/E12) is identical to Example 23c/D2 with the proviso that that E11 is replaced by E12.

Example (23c/D3/E15) is identical to Example 23c/D3 with the proviso that that E11 is replaced by E15.

Example (23c/D4/E19) is identical to Example 23c/D4 with the proviso that E11 is replaced by E19.

Example G/24

A strand of blond undamaged human hair is coloured
24a) with a mixture of 5 g of 6% hydrogen peroxide solution and a composition consisting of 5 g of composition E11and alternatively
24b) first with 5 g of 6% hydrogen peroxide solution, and then with 5 g of composition 11 or
25c) first with 5 g of composition E11 and then with 5 g of 6% hydrogen peroxide solution.

The colouring mixture is allowed to act on the hair for 30 minutes at about 22° C. 10 g of a 2% strength aqueous citric acid gel are then applied to the strand. After contact for 5 minutes, the strand is rinsed thoroughly, shampooed and then dried.

A strong, intense, striking bluish red coloration having good fastness to washing and fastness to rubbing properties is obtained.

Example (24a/E12) is identical to Example 24a with the proviso that E11 is replaced by E12.

Example (24b/E19) is identical to Example 24a with the proviso that E11 is replaced by E19.

Example (24c/E15) is identical to Example 24a with the proviso that E11 is replaced by E15.

Example (24b/E16) is identical to Example 24b with the proviso that E11 is replaced by E16.

Example (24b/E15) is identical to Example 24b with the proviso that E11 is replaced by E15.

Example (24b/E12) is identical to Example 24b with the proviso that E11 is replaced by E12.

Example (25c/E16) is identical to Example 25c with the proviso that E11 is replaced by E16.

Example (25c/E19) is identical to Example 25c with the proviso that E11 is replaced by E19.

Example (25c/E12) is identical to Example 25c with the proviso that E11 is replaced by E12.

Example G/25

A strand of blond undamaged human hair is coloured with 25a) 5 g of a composition according to the following table

| | |
|---|---|
| behentrimonium chloride | 3.8 g |
| cetylalcohol | 4 g |
| phenoxyethanol and isobutylparaben | 0.5 g |
| perfume | 0.1 g |
| Direct Dye of formula (6), wherein $X^-$ is chloride | 0.5 g |
| monoethanolamine | ad pH 6.5 |
| water | ad100 |

The colouring mixture is allowed to act on the hair for 30 minutes at about 22° C. After contact the strand is rinsed and then dried.

A strong, intense, striking coloration having good fastness to washing and fastness to rubbing properties is obtained.

Example (25a/G5) is identical to Example 25a with the proviso that Direct Dye of formula (6), is replaced by Direct Dye of formula (5), wherein $X^-$ is chloride.

Example (25a/G9) is identical to Example 25a with the proviso that Direct Dye of formula (6), is replaced by Direct Dye of formula (9), wherein $X^-$ is iodide.

Example (25a/G13) is identical to Example 25a with the proviso that Direct Dye of formula (6), by Direct Dye of formula (13), wherein $X^-$ is chloride.

Example G/26

26a)

2 g of a composition A according to the following table

| COMPOSITION A | |
|---|---|
| sodium stearat | 11.0 g |
| sluminium distearat | 2.7 g |
| sodium laurylsulfat (Duponol C) | 1.0 g |
| disperse silicic acid (Aerosil 200) | 9.1 g |
| hydroxypropylcellulose | 2.7 g |
| ammoniumpersulfat | 19.0 g |
| sodium metasilicat | 12.0 g |
| disodium salt of ethylentetraminacetic acid | 1.0 g |
| potassium persulfat | 31.5 g | and 3.6 g of a composition B according to the following table

| COMPOSITION B | |
|---|---|
| water | 188 g |
| hydrogenperoxide | 12 g | are mixed to a homogenous mixture. This homogenous mixture is allowed to act on a strand of blond undamaged human hair for 30 minutes at about 22° C. After contact the strand is rinsed, shampooed.

Then the hair is coloured with 5 g of a composition according to the following table

| | |
|---|---|
| behentrimonium chloride | 3.8 g |
| cetylalcohol | 4 g |
| phenoxyethanol and Isobutylparaben | 0.5 g |
| perfume | 0.1 g |
| Direct Dye of formula (6), wherein $X^-$ is chloride | 0.5 g |
| monoethanolamine | ad pH 6.5 |
| Water | ad100 |

The colouring mixture is allowed to act on the hair for 30 minutes at about 22° C. After contact the strand is rinsed and then dried.

A strong, intense, striking coloration having good fastness to washing and fastness to rubbing properties is obtained.

Example (26a/G5) is identical to Example 26a with the proviso that direct dye of formula (6), wherein $X^-$ is chloride is replaced by direct dye of formula (5), wherein $X^-$ is chloride.

Example (26a/G9) is identical to Example 26a with the proviso that direct dye of formula (6), wherein $X^-$ is chloride is replaced by direct Dye of formula (9), wherein $X^-$ is iodide.

Example (26a/G10) is identical to Example 26a with the proviso that direct dye of formula (6), wherein $X^-$ is chloride is replaced by direct dye of formula (10), wherein $X^-$ is chloride.

Example G/27

27a)

2 g of a composition A according to the following table

| COMPOSITION A | |
|---|---|
| sodium stearat | 11.0 g |
| aluminium distearat | 2.7 g |
| sodium laurylsulfat (Duponol C) | 1.0 g |
| disperse silicic acid (Aerosil 200) | 9.1 g |
| hydroxypropylcellulose | 2.7 g |
| ammoniumpersulfat | 19.0 g |
| sodium metasilicat | 12.0 g |
| disodium salt of ethylentetraminacetic acid | 1.0 g |
| potassium persulfat | 31.5 g |
| Direct Dye of formula (6), wherein $X^-$ is chloride | 10 g | and 4 g of a composition B according to the following table

| COMPOSITION B | |
| --- | --- |
| water | 188 g |
| hydrogenperoxide | 12 g | are mixed to a homogenous mixture. This homogenous mixture is allowed to act on a strand of blond undamaged human hair for 30 minutes at about 22° C. After contact the strand is rinsed, shampooed and dried.

Example (27a/G5) is identical to Example 27a with the proviso that direct dye of formula (6), wherein $X^-$ is chloride is replaced by direct dye of formula (5), wherein $X^-$ is chloride Example (27a/G13) is identical to Example 27a with the proviso that direct dye of formula (6), wherein $X^-$ is chloride is replaced by direct dye of formula (13), wherein $X^-$ is chloride.

Example (27a/G9) is identical to Example 27a with the proviso that direct dye of formula (6), wherein $X^-$ is chloride is replaced by direct dye of formula (6), wherein $X^-$ is iodide.

Example G/28

28a)

2 g of a composition A according to the following table

| COMPOSITION A | |
| --- | --- |
| sodium stearat | 11.0 g |
| aluminium distearat | 2.7 g |
| sodium laurylsulfat (Duponol C) | 1.0 g |
| disperse silicic acid (Aerosil 200) | 9.1 g |
| hydroxypropylcellulose | 2.7 g |
| ammoniumpersulfat | 19.0 g |
| sodium metasilicat | 12.0 g |
| disodium salt of ethylentetraminacetic acid | 1.0 g |
| potassium persulfat | 31.5 g |
| Direct Dye of formula (6), wherein $X^-$ is chloride | 10 g | and 4 g of a composition B according to the following table

| COMPOSITION B | |
| --- | --- |
| water | 188 g |
| hydrogenperoxide | 12 g | are mixed to a homogenous mixture. This homogenous mixture is allowed to act on a strand of blond undamaged human hair for 30 minutes at about 22° C. After contact the strand is rinsed and shampooed.

Then the hair is coloured with 5 g of a composition according to the following table

| | |
| --- | --- |
| behentrimonium chloride | 3.8 g |
| cetylalcohol | 4 g |
| phenoxyethanol and Isobutylparaben | 0.5 g |
| perfume | 0.1 g |

-continued

| | |
| --- | --- |
| Direct Dye of formula (6), wherein $X^-$ is chloride | 0.5 g |
| monoethanolamine | ad pH 6.5 |
| water | ad100 |

The colouring mixture is allowed to act on the hair for 30 minutes at about 22° C. After contact the strand is rinsed and then dried.

A strong, intense, striking coloration having good fastness to washing and fastness to rubbing properties is obtained.

Example (28a/G5) is identical to Example 28a with the proviso that direct dye of formula (6), wherein $X^-$ is chloride is replaced by direct dye of formula (5), wherein $X^-$ is chloride.

Example (28a/G10) is identical to Example 28a with the proviso that direct dye of formula (6), wherein $X^-$ is chloride is replaced by direct dye of formula (10), wherein $X^-$ is chloride.

Example (28a/G9) is identical to Example 28a with the proviso that direct dye of formula (6), wherein $X^-$ is chloride is replaced by direct dye of formula (9), wherein $X^-$ is iodide.

Example G/30

30a)

2 g of a composition A according to the following table

| COMPOSITION A | |
| --- | --- |
| sodium stearat | 11.0 g |
| aluminium distearat | 2.7 g |
| sodium laurylsulfat (Duponol C) | 1.0 g |
| disperse silicic acid (Aerosil 200) | 9.1 g |
| hydroxypropylcellulose | 2.7 g |
| ammoniumpersulfat | 19.0 g |
| sodium metasilicat | 12.0 g |
| disodium salt of ethylentetraminacetic acid | 1.0 g |
| potassium persulfat | 31.5 g | is mixed with 2 g of a composition C, and 4 g of a composition B according to the following table

| COMPOSITION B | |
| --- | --- |
| water | 188 g |
| hydrogenperoxide | 12 g | to a homogenous mixture. This homogenous mixture is allowed to act on a strand of blond undamaged human hair for 30 minutes at about 22° C. After contact the strand is rinsed and shampooed.

Then the hair is coloured with 5 g of a composition according to the following table

| | |
| --- | --- |
| behentrimonium chloride | 3.8 g |
| cetylalcohol | 4 g |
| phenoxyethanol and Isobutylparaben | 0.5 g |

-continued

| | |
|---|---|
| perfume | 0.1 g |
| Direct Dye of formula (6), wherein X⁻ is chloride | 0.5 g |
| monoethanolamine | ad pH 6.5 |
| water | ad 100 |

The colouring mixture is allowed to act on the hair for 30 minutes at about 22° C. After contact the strand is rinsed and then dried.

A strong, intense, striking coloration having good fastness to washing and fastness to rubbing properties is obtained.

Example (30a/G5) is identical to Example 30a with the proviso that direct dye of formula (6), wherein X⁻ is chloride is replaced by direct dye of formula (5), wherein X⁻ is chloride.

Example (30a/G10) is identical to Example 30a with the proviso that direct dye of formula (6), wherein X⁻ is chloride is replaced by direct dye of formula (10), wherein X⁻ is chloride.

Example (30a/G9) is identical to Example 30a with the proviso that direct dye of formula (6), wherein X⁻ is chloride is replaced by direct dye of formula (9), wherein X⁻ is iodide.

Example G/31

31a)

2 g of a composition A according to the following table

| COMPOSITION A | |
|---|---|
| sodium stearat | 11.0 g |
| aluminium distearat | 2.7 g |
| sodium laurylsulfat (Duponol C) | 1.0 g |
| disperse silicic acid (Aerosil 200) | 9.1 g |
| hydroxypropylcellulose | 2.7 g |
| ammoniumpersulfat | 19.0 g |
| sodium metasilicat | 12.0 g |
| disodium salt of ethylentetraminacetic acid | 1.0 g |
| potassium persulfat | 31.5 g | is mixed with a 2.0 g of a composition E11 and 6 g of a composition B according to the following table

| COMPOSITION B | |
|---|---|
| water | 188 g |
| hydrogenperoxide | 12 g | to a homogenous mixture. This homogenous mixture is allowed to act on a strand of blond undamaged human hair for 30 minutes at about 22° C. After contact the strand is rinsed, shampooed and dried.

Example (31a/E12) is identical to Example 31a with the proviso that E11 is replaced by E12.

Example (31b/E15) is identical to Example 31a with the proviso that E11 is replaced by E15.

Example (31c/E19) is identical to Example 31a with the proviso that E11 is replaced by E19.

Example G/32

32a)

2 g of a composition A according to the following table

| COMPOSITION A | |
|---|---|
| sodium stearat | 11.0 g |
| aluminium distearat | 2.7 g |
| sodium laurylsulfat (Duponol C) | 1.0 g |
| disperse silicic acid (Aerosil 200) | 9.1 g |
| hydroxypropylcellulose | 2.7 g |
| ammoniumpersulfat | 19.0 g |
| sodium metasilicat | 12.0 g |
| Di sodium salt of ethylentetraminacetic acid | 1.0 g |
| potassium persulfat | 31.5 g | is mixed with a 2.0 g of a COMPOSITION C as given in example G and 2.0 g of a direct dye of formula (6), wherein X⁻ is chloride and 8 g of a COMPOSITION B according to the following table

| COMPOSITION B | |
|---|---|
| water | 188 g |
| hydrogenperoxide | 12 g | to a homogenous mixture. This homogenous mixture is allowed to act on a strand of blond undamaged human hair for 30 minutes at about 22° C. After contact the strand is rinsed, shampooed and dried.

Example (32a/G5) is identical to Example 32a with the proviso that direct dye of formula (6), wherein X⁻ is chloride is replaced by direct dye of formula (5), wherein X⁻ is chloride.

Example (32a/G13) is identical to Example 32a with the proviso that direct dye of formula (6), wherein X⁻ is chloride is replaced by direct dye of formula (13), wherein X⁻ is chloride.

Example (32a/G9) is identical to Example 32a with the proviso that direct dye of formula (6), wherein X⁻ is chloride is replaced by direct dye of formula (9), wherein X⁻ is iodide.

Example G/33

33a)

| Composition (A') | |
|---|---|
| polyglycerol alcohol with 2 mols of glycerol | 4.0 g |
| polyglycerol alcohol with 4 mols of glycerol of 78% (M.A.) | 5.69 g |
| oil acid | 3.0 g |
| oleic amine with 2 mols ethylenoxide available from ETHOMEEN O12 from AKZO | 7.0 g |
| laurylamine succinamate of diethylaminopropylene, salt of sodium with 55%. | 3.0 g |
| oil alcohol | 5.0 g |
| diethynolamide of oil acid | 12.0 g |
| propylenglycol | 3.5 g |

| | |
|---|---|
| ethylenalcohol | 7.0 g |
| monobutylether of diethylenglycol | 0.5 g |
| monomethylether of propylenglycol | 0.5 g |
| sodium metabisulfite as solution a 35% | 0.455 g |
| ammonium acetate | 0.8 g |
| paraphenylendiamine | 0.35 g |
| 1,3-dihydroxybenzene | 0.4 g |
| 3-amino phenol | 0.03 g |
| 2,4-diamino-1-(β-hydroxyethyloxy)benzene, 2HCl | 0.012 g |
| 1,3-bis-[(4-aminophenyl)2-hydroxyethyl)-amino]-2-propanol, 4HCl | 0.037 g |
| 1,3-dihydroxy-2-methyl-benzene | 0.2 g |
| antioxidant | qs |
| parfume | qs |
| ammonia 20% of NH$_3$ | 10.0 g |
| water | 100 g |
| Composition (B') | |
| direct dye of formula (6), wherein X$^-$ is chloride in powder form | 20 g |
| oil of parafine | 3 g |
| cationic polymeric powder (Merquat 280 Dry de Calgon) | 10 g |
| sawdust | 100 g |
| Composition (C'): | |
| hydrogenperoxide 20% by volume | |

Just before the colouration of human hair a mixture of 1 equivalent of weight of Composition (A'), 01 equivalent of weight of composition (B') and 1 equivalent of weight of composition (C') is mixed.

The pH of the mixture is adjusted to 9.8.

The colouring mixture is applied on human grey hair. This mixture is allowed to act on a strand of blond undamaged human hair for 30 minutes. After contact the strand is rinsed, shampooed and dried.

Example (33a/G5) is identical to Example 33a with the proviso that direct dye of formula (6), wherein X$^-$ is chloride is replaced by direct dye of formula (5), wherein X$^-$ is chloride.

Example (33a/G13) is identical to Example 33a with the proviso that direct dye of formula (6), wherein X$^-$ is chloride is replaced by direct dye of formula (13), wherein X$^-$ is chloride.

Example (33a/G9) is identical to Example 33a with the proviso that G6 is replaced by direct dye of formula (9), wherein X$^-$ is iodide.

Example G/34

34a)

| Composition (B') | |
|---|---|
| direct dye of formula (6), wherein X$^-$ is chloride in powder form | 20 g |
| Oil of parafine | 3 g |
| cationic polymeric powder (Merquat 280 Dry de Calgon) | 10 g |
| sawdust | 100 g |
| Composition (C'): | |
| hydrogenperoxide 20% by volume | 100 g |

Just before the colouration of human hair a mixture of 1 equivalent of weight of Composition (B'), and 1 equivalent of weight of composition (C') is mixed.

The pH of the mixture is adjusted to 9.8.

The colouring mixture is applied on human grey hair. This mixture is allowed to act on a strand of blond undamaged human hair for 30 minutes. After contact the strand is rinsed, shampooed and dried.

Example (34a/G5) is identical to Example 34a with the proviso that direct dye of formula (6), wherein X$^-$ is chloride is replaced by direct dye of formula (5), wherein X$^-$ is chloride.

Example (34a/G9) is identical to Example 34a with the proviso that direct dye of formula (6), wherein X$^-$ is chloride is replaced by direct dye of formula (9), wherein X$^-$ is iodide.

Example (34a/G10) is identical to Example 34a with the proviso that direct dye of formula (6), wherein X$^-$ is chloride is replaced by direct dye- of formula (10), wherein X$^-$ is chloride.

Example G/35

35a)

| Composition (B') | |
|---|---|
| direct dye of formula (6), wherein X$^-$ is chloride, powder form | 20 g |
| Oil of parafine | 3 g |
| cationic polymeric powder (Merquat 280 Dry de Calgon) | 10 g |
| sawdust | 100 g |
| Composition (C'): | |
| hydrogenperoxide 20% by volume | 100 g |

Just before the colouration of human hair a mixture of 1 equivalent of weight of Composition (B'), and 1 equivalent of weight of composition (C') is mixed.

The pH of the mixture is adjusted to 9.8 with ammonia 20% by volume.

The colouring mixture is applied on human grey hair. This mixture is allowed to act on a strand of blond undamaged human hair for 30 minutes. After contact the strand is rinsed, shampooed and dried.

Example (35a/G13) is identical to Example 35a with the proviso that direct dye of formula (6), wherein X$^-$ is chloride is replaced by direct dye of formula (13), wherein X$^-$ is chloride.

Example (35a/G9) is identical to Example 35a with the proviso that direct dye of formula (6), wherein X$^-$ is chloride is replaced by direct dye of formula (9), wherein X$^-$ is iodide.

Example (35a/G5) is identical to Example 35a with the proviso that direct dye of formula (6), wherein X$^-$ is chloride is replaced by direct dye of formula (5), wherein X$^-$ is chloride.

Example 36

105 g of Phenyl hydrazine 98% is added with stirring to 200 ml Isopropanol. 124 g of 4-acetyl-pyridine is dropped in during 5 minutes. Then the temperature is raised to 345 K, and the reaction mixture stirred 3 hour at this temperature. A solution of hydrazone is obtained. This solution is added with stirring to 500 g water at a temperature in the range of 393 to 398 K. Then, 313,4 g dimethylsulphate 100% is added in 3–5 hours by a constant rate and the pH is maintained at 10.5 by addition of a 36% sodium hydroxide solution. The temperature is maintained at 393–398 K by cooling. The reaction mass is stirred for 60 minutes at a pH in the range of pH 6 to 7. The desired product is crystallized in the reaction mass and is filtered. Then, the filter residue is washed with 150 ml of water and dried in vacuum to obtain 238 g of a brown solid product of the below given formula. The product is recrystallized twice from 2-propanol.

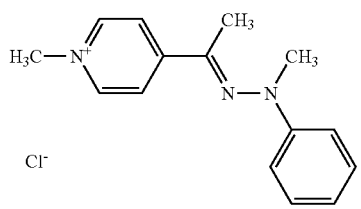

Example 37

125 g of N-methyl-phenyl hydrazine 100% is added with stirring to 400 ml Isopropanol. 124 g of 4-acetyl-pyridine is dropped in during 5 minutes. Then, the temperature is raised to 345 K, and the mixture is stirred for 6 hours at this temperature. After this time, 133 g benzylchloride is added. The temperature maintained at 345 K during the following 15 hours and the mixture stirred. Afterwards, the solution is slowly cooled till crystallization is initiated with seeding and then the crystallization is advanced by cooling to room temperature. The slurry is separated by filtration. The filter residue is washed with 3×50 ml of 2-propanol and then, dried in vacuum to obtain 304 g of an orange solid product. The product is recrystallized twice from 2-propanol getting 254 g purified product of the below given formula

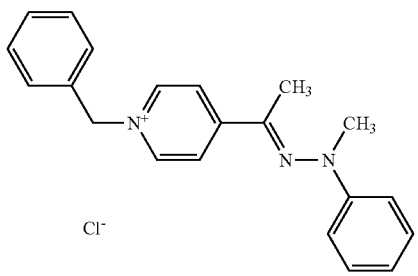

Example 38

105 g of Phenyl hydrazine 98% is added with stirring to 200 ml isopropanol. Then, 124 g of 2-acetyl-pyridine is dropped in during 5 minutes. The temperature is raised then to 345 K, and the reaction mixture stirred 10 hours at this temperature. A solution of hydrazone is obtained. This solution is added with stirring to 500 g water at a temperature in the range of 393 to 398 K. Then, 343,4 g dimethylsulphate 100% is added in 3–5 hours by a constant rate in a temperature range of 393 to 398 K, and the pH is maintained at 10.5 by addition of a 36% sodium hydroxide solution. After the addition, the reaction mass is stirred for 60 minutes at pH 6–7. The crystallized product is filtered, and then is washed with 150 ml of water and afterwards dried in vacuum to obtain 208 g of a brown solid product of the below given formula. The product is recrystallized twice from 2-propanol.

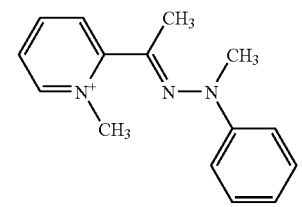

Example 39

105 g of Phenyl hydrazine 98% is added with stirring to 400 ml isopropanol. 124 g of 3-acetyl-pyridine is dropped in during 5 minutes. Then, the temperature is raised to 345 K, and the reaction mixture stirred 5 hours at this temperature. Afterwards, 233 g methyliodide is added. Then, the mixture is stirred by 293 K during 15 hours. Afterwards, the slurry is separated by filtration and the filter residue is washed with 3×50 ml of 2-propanol and dried in vacuum to obtain 360 g of a orange solid product. The product is recrystallized twice from 2-propanol getting 294 g purified product of the below given formula

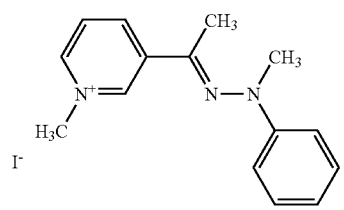

Example 40

125 g of N-methyl-phenyl hydrazine 98% is added with stirring to 400 ml isopropanol. 124 g of 3-acetyl-pyridine is dropped in during 5 minutes. Then, the temperature is raised to 345 K, and the reaction mixture stirred 4 hour at this temperature. Then, 133 g Benzylchloride is added. Afterwards, the mixture is stirred at 345 K during 15 hours. The solution is cooled slowly till crystallization is initiated with seeding and later cooled to room temperature. The slurry is separated by filtration, and the filter residue is washed with 3×50 ml of 2-propanol and dried in vacuum to obtain 304 g of an orange solid product. The product is recrystallized twice from 2-propanol getting 254 g purified product of the below given formula

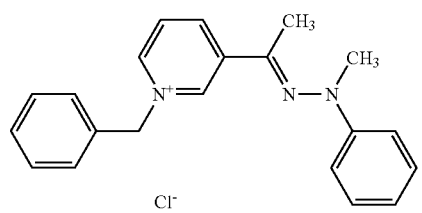

Example 41

A strongly alkaline 10% solution of a non-ionic surfactant (Plantaren 2000, Henkel) is adjusted to pH 9.5 using citric acid. 0.1% of the dye of formula

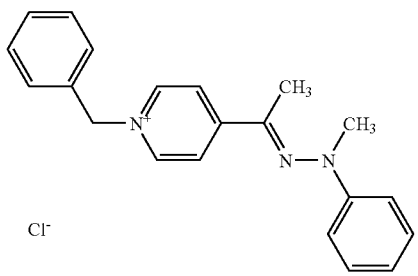

is dissolved therein, and a strand of human hair, bleached white, is treated with the dye solution at room temperature. After only a short period of time, the strand is dyed an orange shade, which is still very intensive even shampooing ten times. The dye also has a strong affinity to undamaged hair. In that case, too, the wash fastness is very good. The light fastness on damaged and undamaged hair is excellent. The perm fastness is on un- and damaged hair very good as well.

Example 42

A 10% solution of a non-ionic surfactant (Plantaren 2000, Henkel) is adjusted to pH 5.5 using citric acid. 0.1% of the dye of formula

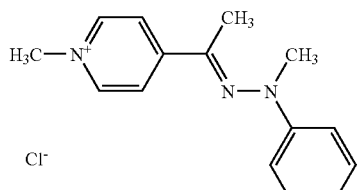

is dissolved therein and a strand of middle blonde undamaged human hair is treated with the dye solution at room temperature. After only a short period of time, the strand has been dyed a yellow shade, which has a good wash, perm and light fastness.

Example 43

A dye emulsion, containing 0.1% of the dye according to the invention of formula

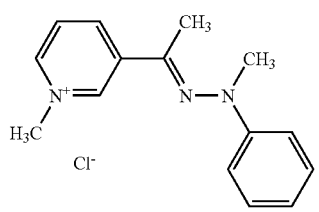

3.5% cetearyl alcohol

% ceteareth 80

0.5% glyceryl mono-di-stearate 3.0% stearamide DEA 1.0% stearamphopropyl sulfonate 0.5% polyquarternium-6 and water ad 100% is applied for 30 minutes, at room temperature, to bleached human hair, and rinsed. The result is a very attractive vibrant yellow dyeing with good fastnesses.

Example 44

A dye emulsion, containing 1% of the dye of example 42, pH=9.8

| | |
|---|---|
| cetylstearylalcohol | 11.00 |
| oleth-5 | 5.0 |
| oleic acid | 2.5 |
| stearic acid monoethanolamide | 2.5 |
| coco fatty acid monoethanolamide | 2.5 |
| sodium laurylsuphate | 1.7 |
| 1,2-propanediol | 1.0 |
| ammoniumchloride | 0.5 |
| EDTA, tetrasodiumsalt | 0.2 |
| perfume | 0.4 |
| comproteinhydrolysate | 0.2 |
| silica | 0.1 | is mixed with the same weight of 6% hydrogen peroxide solution and the mixture is immediately applied to a tress of brown hair. After 30 minutes the tress is rinsed, shampooed, rinsed and dried.

The color result is a very brilliant yellow shade.

Example 44

A dye emulsion, containing 0.5% of the dye of example 42, pH=9.8

| | |
|---|---|
| cetylstearylalcohol | 11.00 |
| oleth-5 | 5.0 |
| oleic acid | 2.5 |
| stearic acid monoethanolamide | 2.5 |
| coco fatty acid monoethanolamide | 2.5 |
| sodium laurylsuphate | 1.7 |
| sodiumsulphite | 1.0 |
| ascorbic acid | 0.5 |
| 1,2-propanediol | 1.0 |
| ammoniumchloride | 0.5 |
| EDTA, tetrasodiumsalt | 0.2 |
| perfume | 0.4 |
| comproteinhydrolysate | 0.2 |
| silica | 0.1 |
| toluene-2,5-diamine sulfate | 0.07 |
| resorcinol | 0.02 |
| 2-amino-6-chloro-4-nitrophenol | 0.01 |
| 4-amino-m-cresol | 0.03 |
| 2-amino-3-hydroxypyridine | 0.001 | is mixed with the same weight of 6% hydrogen peroxide solution and the mixture is immediately applied to a tress of brown hair. After 30 minutes the tress is rinsed, shampooed, rinsed and dried.

The color result is a very brilliant reddish-golden shade.

Example 45

A strongly alkaline 10% solution of a non-ionic surfactant (Plantaren 2000, Henkel) is adjusted to pH 9.5 using citric acid. 0.2% of the dye of application example 41 and 0.1% of the dye formula

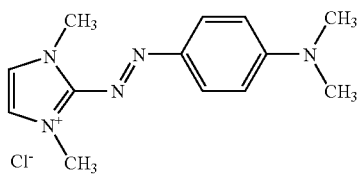

are dissolved therein and a strand of middle blonde undamaged human hair is treated with the dye solution at room temperature. After only 10 minutes, the strand has been dyed an intensive orange shade, which has a good wash, perm and light fastness.

Example 46

A strongly alkaline 10% solution of a non-ionic surfactant (Plantaren 2000, Henkel) is adjusted to pH 9.5 using citric acid. 0.2% of the dye of example 41 and 0.1% of the dye formula

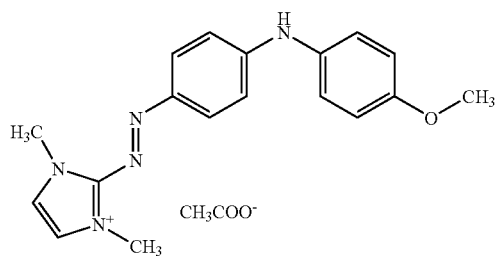

are dissolved therein and a strand of dark blonde undamaged human hair is treated with the dye solution at room temperature. After 20 minutes, the strand has been dyed an intensive red-copper shade, which has a good wash, perm and light fastness.

Example 47

A strand of bleached human hair is treated with 10 g of a dye composition having a pH of 9.8, comprising 5 g of a 6% hydrogen peroxide solution and 5 g of a composition A given below in example 47:

| Composition A | |
|---|---|
| oleic acid | 10.0 |
| toluene-2,5-diamine sulfate | 0.07 |

| Composition A | |
|---|---|
| resorcinol | 0.02 |
| 2-amino-6-chloro-4-nitrophenol | 0.01 |
| 4-amino-m-cresol | 0.03 |
| 2-amino-3-hydroxypyridine | 0.001 |
| sodium sulfit | 1.0 |
| ascorbinic acid | 0.5 |
| water | Ad 100 |

After 15 minutes, 10 g of a 12,5% citric acid gel, comprising the dye of example 41, is applied on the hair and combed, so that the hair has a pH of 7. After 15 minutes the hair is washed with water, rinsed and dried. The dyed strand has an intensive golden shade, which has a good wash and light fastness.

Example 48

A strand of middle blonde human hair is dyed with 10 g of a composition having a pH of 9.8, which is obtained by mixing 5 g of 6% hydrogen peroxide solution and 5 g of a composition A given below in example 48:

| Composition A | |
|---|---|
| oleic acid | 10.0 |
| toluene-2,5-diamine sulfate | 0.07 |
| resorcinol | 0.02 |
| 2-amino-6-chloro-4-nitrophenol | 0.01 |
| 4-amino-m-cresol | 0.03 |
| 2-amino-3-hydroxypyridine | 0.001 |
| sodium sulfite | 1.0 |
| ascorbinic acid | 0.5 |
| water | ad 100 |

After 15 minutes, the pH of the hair is adjusted to pH 5 by addition of citric acid. Then, 5 g of a 12,5% citric acid gel, comprising the dye of example 41, is applied on the hair and combed, so that the hair has a pH of 7. After 15 minutes the hair is washed with water, rinsed and dried. The strand has been dyed in an intensive golden shade, which has a good wash and light fastness.

Example 49

A strand of bleached human hair is dyed with 10 g of a composition having a pH of 9.8, which is obtained by mixing 5 g of 6% hydrogen peroxide solution and 5 g of a composition A given in example 48.

After 15 minutes, the pH of the hair is adjusted to pH 5 by addition of citric acid. Then, 5 g of a 12,5% citric acid gel, comprising the dye of example 42, is applied on the hair and combed, so that the hair has a pH of 7. After 15 minutes the hair is washed with water, rinsed and dried. The strand has been dyed in an intensive golden shade, which has a good wash and light fastness.

The invention claimed is:

1. Cationic dye of formula (1), (2) or (3)

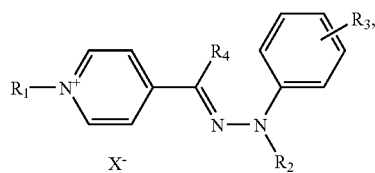
(1)

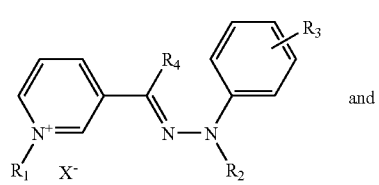
(2)

and

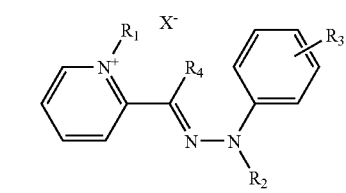
(3)

wherein
- $R_1$ and $R_2$ are each independently of the other a $C_1$–$C_8$alkyl radical or an unsubstituted or substituted benzyl radical,
- $R_3$ is hydrogen, $C_1$–$C_8$alkyl, $C_1$–$C_8$alkoxy, cyanide or halide, and
- $R_4$ is a $C_1$–$C_8$alkyl radical or an unsubstituted or substituted aryl radical, and
- $X^-$ is an anion.

2. Cationic dye according to claim 1, wherein
$R_1$ and $R_2$ are each independently of the other a methyl radical or an unsubstituted or substituted benzyl radical.

3. Cationic dye according to claim 1, wherein
$R_1$ and $R_2$ are each independently of the other a methyl radical or an unsubstituted or substituted benzyl radical, and
$R_4$ is a methyl radical.

4. Cationic dye according to claim 1 of formula (4), (5'), (6), (7), (8), (9), (10), (11), (12), (13) or (14)

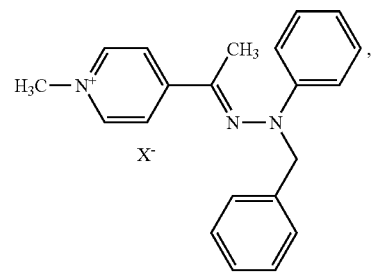
(4)

-continued

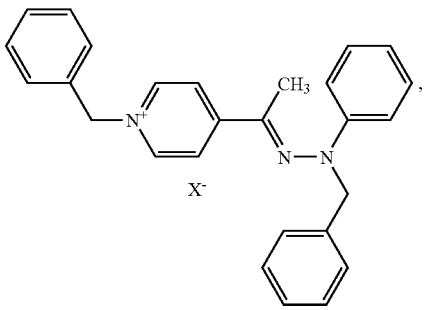
(5')

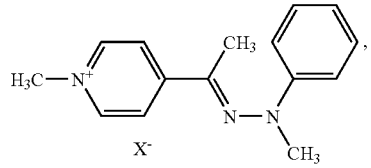
(5)

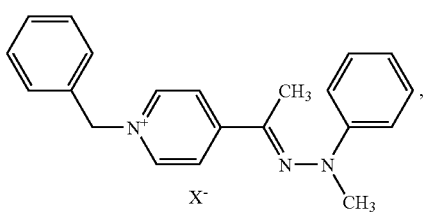
(6)

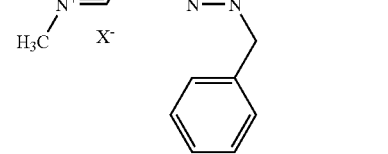
(7)

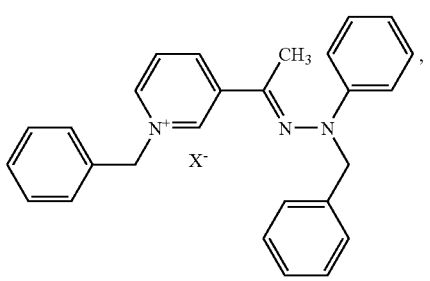
(8)

(9)

-continued

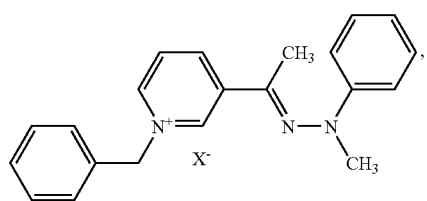 (10)

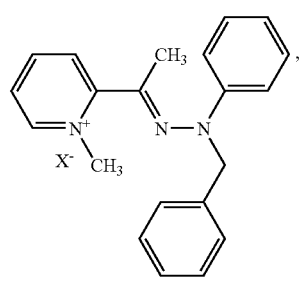 (11)

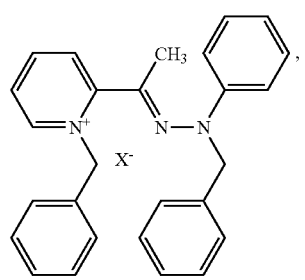 (12)

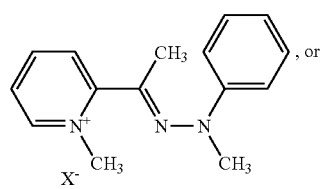 (13)

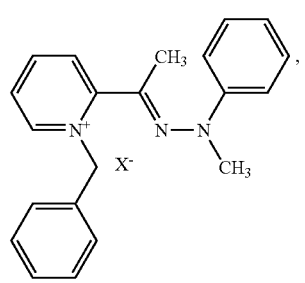 (14)

wherein
X⁻ is an anion.

5. A process for the preparation of cationic dyes of formula (1), (2) or (3) as defined above in claim 1, which comprises reacting a phenylhydrazine of formula (15)

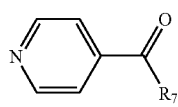 (15)

wherein
$R_5$ is hydrogen, a $C_1$–$C_8$alkyl radical or an unsubstituted or substituted benzyl radical, and
$R_6$ is hydrogen, $C_1$–$C_8$alkyl, $C_1$–$C_8$alkoxy, cyanide or halide, with a
a) 4-pyridylketone of formula (16)

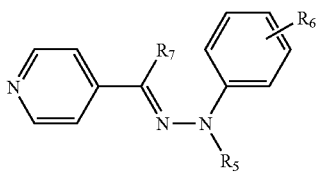 (16)

wherein
$R_7$ is a $C_1$–$C_8$alkyl radical or an unsubstituted or substituted aryl radical, to form a hydrazone of formula (17)

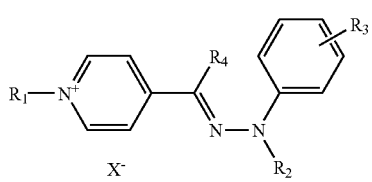 (17)

wherein
$R_5$ is hydrogen, a $C_1$–$C_8$alkyl radical or an unsubstituted or substituted benzyl radical,
$R_6$ is hydrogen, $C_1$–$C_8$alkyl, $C_1$–$C_8$alkoxy, cyanide or halide, and
$R_7$ is a $C_1$–$C_8$alkyl radical or an unsubstituted or substituted aryl radical, and
then reacting the latter compound of formula (17) with an alkylating or benzylating agent to form a compound of formula (1)

(1)

wherein
R₁ and R₂ are each independently of the other a C₁–C₈alkyl radical or an unsubstituted or substituted benzyl radical,
R₃ is hydrogen, C₁–C₈alkyl, C₁–C₈alkoxy, cyanide or halide, and
R₄ is a C₁–C₈alkyl radical or an unsubstituted or substituted aryl radical, and
X⁻ is an anion; or,
which process comprises reacting a phenylhydrazine of formula (15) with
b) 3-pyridylketone of formula (18)

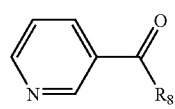
(18)

wherein
R₈ is a C₁–C₈alkyl radical or an unsubstituted or substituted aryl radical, to form a hydrazone of formula (19)

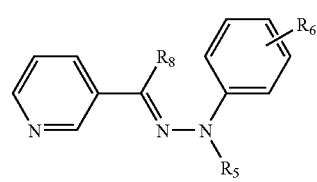
(19)

R₅ is hydrogen, a C₁–C₈alkyl radical or an unsubstituted or substituted benzyl radical,
R₆ is hydrogen, C₁–C₈alkyl, C₁–C₈alkoxy, cyanide or halide, and
R₈ is a C₁–C₈alkyl radical or an unsubstituted or substituted aryl radical, and
then reacting the latter compound of formula (19) with an alkylating or benzylating agent to form a compound of formula (2)

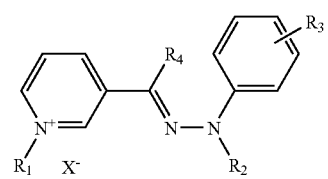
(2)

wherein
R₁ and R₂ are each independently of the other a C₁–C₈alkyl radical or an unsubstituted or substituted benzyl radical,
R₃ is hydrogen, C₁–C₈alkyl, C₁–C₈alkoxy, cyanide or halide, preferably hydrogen, and
R₄ is a C₁–C₈alkyl radical or an unsubstituted or substituted aryl radical, and
X⁻ is an anion; or,
which process comprises reacting a phenylhydrazine of formula (15) with c) 2-pyridylketone of formula (20)

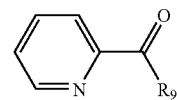
(20)

wherein
R₉ is a C₁–C₈alkyl radical or an unsubstituted or substituted aryl radical, to form a hydrazone of formula (21)

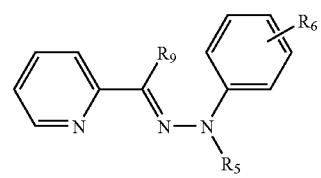
(21)

R₅ is hydrogen, a C₁–C₈alkyl radical or an unsubstituted or substituted benzyl radical,
R₆ is hydrogen, C₁–C₈alkyl, C₁–C₈alkoxy, cyanide or halide, and
R₉ is hydrogen, a C₁–C₈alkyl radical or an unsubstituted or substituted aryl radical, and
then reacting compound of formula (21) with an alkylating or benzylating agent to form a compound of formula (3)

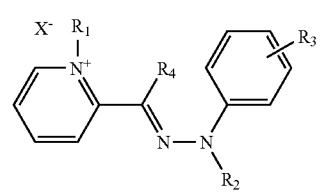
(3)

wherein
R₁ and R₂ are each independently of the other a C₁–C₈alkyl radical or an unsubstituted or substituted benzyl radical,
R₃ is hydrogen, C₁–C₈alkyl, C₁–C₈alkoxy, cyanide or halide, preferably hydrogen, and
R₄ is a C₁–C₈alkyl radical or an unsubstituted or substituted aryl radical, and
X⁻ is an anion.

6. A composition comprising at least a single cationic dye of formula (1), (2) or (3) as defined in claim 1, and an excipient.

7. A composition according to claim 6 comprising in addition at least a single further direct dye and/or an oxidative agent.

8. A composition according to claim 6 comprising in addition at least a single oxidative dye and/or at least a single oxidative dye and an oxidative agent.

9. Composition according to claim 6, in the form of a shampoo, gel or emulsion.

10. A method of dyeing hair that comprises bringing into contact with hair a cationic dye of formula (1), (2) or (3) according to claim 1, and, optionally, a further dye.

11. A method according to claim 10 for dyeing or tinting human hair.

12. A method for dyeing human hair or strands according to claim 10, that comprises contacting the hair with a cationic dye of formula (1), (2) or (3) and an oxidative agent and optionally a further direct dye.

13. A method for dyeing human hair according to claim 12, that comprises contacting the hair with a cationic dye of formula (1), (2) or (3) and at least a single oxidative dye; or contacting the hair with a cationic dye of formula (1), (2) or (3) and at least a single oxidative dye and an oxidative agent.

* * * * *